(12) United States Patent
Weinberg et al.

(10) Patent No.: US 7,800,070 B2
(45) Date of Patent: Sep. 21, 2010

(54) QUANTUM PHOTODETECTORS, IMAGING APPARATUS AND SYSTEMS, AND RELATED METHODS

(75) Inventors: Irving Weinberg, Bethesda, MD (US); Valeri Saveliev, Hamburg (DE)

(73) Assignee: Quantum Molecular Technologies, Inc., Ontario (CA)

( * ) Notice: Subject to any disclaimer, the term of this patent is extended or adjusted under 35 U.S.C. 154(b) by 187 days.

(21) Appl. No.: 11/783,613

(22) Filed: Apr. 10, 2007

(65) Prior Publication Data
US 2008/0156993 A1 Jul. 3, 2008

Related U.S. Application Data

(60) Provisional application No. 60/790,529, filed on Apr. 10, 2006, provisional application No. 60/802,504, filed on May 23, 2006, provisional application No. 60/858,415, filed on Nov. 13, 2006.

(51) Int. Cl.
*G01T 1/164* (2006.01)
*G01T 1/24* (2006.01)

(52) U.S. Cl. .............................. 250/363.03; 250/370.06

(58) Field of Classification Search ............ 250/363.03, 250/363.04, 367, 214 R, 363.06; 324/318
See application file for complete search history.

(56) References Cited

U.S. PATENT DOCUMENTS

| | | | |
|---|---|---|---|
| 4,647,781 A | | 3/1987 | Takagi et al. |
| 5,025,151 A | | 6/1991 | Melcher |
| 5,453,623 A | | 9/1995 | Wong et al. |
| 5,484,750 A | | 1/1996 | Greskovich et al. |
| 5,600,145 A | | 2/1997 | Plummer |
| 5,864,146 A | * | 1/1999 | Karellas .................... 250/581 |
| 6,281,504 B1 | | 8/2001 | Takayama et al. |
| 6,630,077 B2 | | 10/2003 | Shiang et al. |
| 6,793,848 B2 | | 9/2004 | Vartuli et al. |
| 6,885,827 B2 | | 4/2005 | Shushakov et al. |
| 7,008,558 B2 | | 3/2006 | Vartuli et al. |
| 7,084,403 B2 | | 8/2006 | Srivastava et al. |
| 7,085,502 B2 | | 8/2006 | Shushakov et al. |
| 7,115,875 B1 | * | 10/2006 | Worstell ................ 250/363.03 |
| 7,535,011 B2 | | 5/2009 | Chowdhury et al. |
| 2003/0080298 A1 | * | 5/2003 | Karplus et al. ........... 250/370.1 |
| 2005/0006589 A1 | * | 1/2005 | Joung et al. ............ 250/370.09 |
| 2005/0012033 A1 | | 1/2005 | Stern et al. |
| 2005/0133725 A1 | * | 6/2005 | Jiang et al. ............. 250/370.11 |

(Continued)

OTHER PUBLICATIONS

Motomura et al., "Development of a Lead X-ray Compensation Method in Simultaneous T1-201 Spect & ... ", IEEE Transactions on Nuclear Science, vol. 44, No. 6 (Dec. 1997), 2459-2464.

(Continued)

*Primary Examiner*—David P Porta
*Assistant Examiner*—Faye Boosalis
(74) *Attorney, Agent, or Firm*—Berenato & White, LLC

(57) ABSTRACT

A camera sub-module is provided for providing tomographic imaging of radiation emissions generated internally by a body. The camera sub-module includes a radiation-emitting layer having a radioactive source for emitting transmission emissions, and at least one radiation-detection layer for contemporaneously detecting and permitting differentiation between the transmission emissions and emissions generated internal to an imaged body administered with a positron-emitting radiotracer. Also provided herein are imaging systems, scanners, and other apparatus and methods.

43 Claims, 17 Drawing Sheets

U.S. PATENT DOCUMENTS

2006/0027742 A1* 2/2006 Srivastava et al. ............ 250/256
2006/0124832 A1* 6/2006 Harmon et al. .......... 250/214 R

OTHER PUBLICATIONS

V. Golovin, V. Saveliev, Novel type of avalance photodetector with Geiger mode operation, Nuclear Instruments and Methods in Physics Research A 518 (2004) 560-564.

Lempicki et al., LuAlO3:Ce and Other Aluminate Scintillators, IEEE Transactions on Nuclear Science, pp. 307-311 (1995).

Lempicki et al., LuAlO3:Ce and Other Aluminate Scintillators, IEEE Transactions on Nuclear Science, vol. 42, No. 4, pp. 280-284 (1995).

Nikl et al., Traps and Timing Characteristics of LuAG:Ce3+ Scintillator, Phys. Stat. Sol. 181 (2000).

Li et al., Fabrication of Transparent Cerium-Doped Lutetium Aluminum Garnet . . . Method, J. Am. Ceram. Soc. 88 [11] 3226-3228 (2005).

Moehrs et al., A detector head design for small-animal PET with silicon photomultipliers (SiPM), Phys. Med. Biol. 51, 1113-1127 (2006).

Zappa, SPADA: Single-Photon Avalance Diode Arrays, IEEE Photonics Technology Letters, vol. 17, No. 3, 657-59 (2005).

Aull, et al., Geiger-Mode Avalanche Photodiodes for Three-Dimensional Imaging, Lincoln Lab. Journal, vol. 13, No. 2, 335-50 (2002).

V. Saveliev, et al., Avalanche Photodiode . . . Needle Metal-Resistor-Semiconductor Structures, Oral Presentation, 7th European Symposium on Semiconductor Detectors (1995) 1-9.

V. Saveliev et al., Silicon avalanche photodiodes . . . metal-resistor-semiconductor MRS Structures, Nuclear Instruments and Methods in Physics Research A 442 (2000) 223-229.

V. Saveliev, The recent development and study of silicon photomultiplier, Nuclear Instruments and Methods in Physics Research A 535 (2004) 528-32.

Silicon-Photomultiplier: Recent Developments and Results, Oral Presentation IEEE, NSS2004, pp. 1-20 (2005).

D. McElroy, et al., Evaluation of silicon photomultipliers: A promising . . . compatible PET, Nuclear Instruments and Methods in Physics Research A 571 (2007) 106-09.

V. Saveliev, SiPM Resent Development and Applications, Oral Presentation at 4th BEAUNE Conference on New Developments in Photodetectors (2005, France), pp. 1-24.

V. Saveliev, SiPM Resent Development and Study, Oral Presentation on IEEE 2005 (2005), pp. 1-20.

A.G. Stewart, et al., Study of the Properties of New SPM Detectors, Proceedings of SPIE: Semiconductor Photodetectors III, vol. 6119 (2006) 10 pages.

Hain et al., Avalanche Photodiode on the Base of Metal-Resistor-Semiconductor Structures.

Hamamatsu, MPPC Multi-Pixel Photon Counter, Nuclear Science Symposium, Oct. 29 to Nov. 4 2006, 1-14 pgs, San Diego, California, USA.

Jackson et al., A Novel Silicon Geiger-Mode Avalanche Photodiode, Proceedings IEDM, 32-2, Dec. 2002.

* cited by examiner

QUANTUM PHOTODETECTORS, IMAGING APPARATUS AND SYSTEMS, AND RELATED METHODS

CROSS-REFERENCE TO RELATED APPLICATIONS

This application claims the benefit of priority of Provisional Application No. 60/790,529 filed Apr. 10, 2006 entitled "Imaging Apparatus and Sub-Module for PET and SPECT with Attenuation Events, and Related Method," Provisional Application No. 60/802,504 filed May 23, 2006 entitled "Quantum Detectors, Arrays, Meta-Arrays, and Related Detector-Readout Systems and Methods," and Provisional Application No. 60/858,415 filed Nov. 13, 2006 and entitled "Low Cost, High Performance PET Scanner," the complete disclosures of each of which is incorporated herein by reference.

FIELD OF THE INVENTION

The present invention relates to camera sub-modules, imaging apparatus, systems, and methods that provide information about radiation emission (e.g., positron emission tomography, or "PET") and optionally geographic or anatomic information (e.g., x-ray computed tomography, or "CT") regarding an object such as a body, body part, or an instrument, including an instrument introduced into a body or body part.

BACKGROUND OF THE INVENTION

PET Imaging

Internal diagnostic examinations for medical purposes are often conducted using a procedure known as positron emission tomography, also commonly referred to as PET imaging. PET imaging involves the administration of a radioactive substance (or radiotracer) into the body of a patient, such as a living human being, animal, or other object of interest. Radioactive atoms present in these substances are selected from, for example, carbon-11, fluorine-18, oxygen-15, and nitrogen-13, each of which has a short decay time. The radioactive substance emits particles known as positrons, which collide with electrons in the patient's tissue. The electrons and positrons undergo what is known as electron-positron annihilations, each generating a pair of gamma rays at the collision site to emit the gamma rays in coincidence from the site in opposite directions.

After the radioactive substance has been administered, the patient or object of interest is placed on a flat table that moves incrementally through a detection apparatus, commonly referred to as a scanner. Gamma rays emitted in opposite directions due to the electron-positron annihilations in the patient or object exit the body, and are detected by the PET scanner, and more particularly by sub-modules of gamma ray detectors arranged in an annular array.

The gamma-ray detectors have scintillation crystals which convert the gamma rays into photons of light. Photosensors (e.g., photomultiplier tubes) of the gamma-ray detectors convert the photons of light into electric signals. A computer records the locations of each detected photon, and identifies pairs of simultaneous photon detections. The location and timing of the identified pairs are used to generate internal physiological images of internal body parts, foreign bodies, and structures within the patient, such as organs and tumors. The images are useful, for example, in the diagnosis of various diseases and medical conditions, such as cancer and coronary artery diseases, as well as in the evaluation of on-going treatment procedures regimes, such as chemotherapy response monitoring.

SPECT Imaging

Single photon emission computed tomography, also commonly referred to as SPECT imaging, is similar to PET, but uses radioactive substances such as technetium-99 and iodine-123 emitting a single gamma ray instead of a gamma ray pair. The gamma-ray detector receiving the single gamma ray typically has a collimator for ascertaining the direction vector of the gamma ray. There have been theoretical studies suggesting that a double-detector method (so-called Compton camera) could be used to determine the direction vector of the gamma ray, but it is believed by applicant that no such systems have yet been constructed for clinical use. Additionally, Compton cameras typically ignore events with low angular scatter because the gamma-ray detectors employed in Compton cameras have difficulties measuring the low energy losses associated with low angular scatter. Although SPECT imaging provides less detailed images than PET imaging, the images obtained using SPECT can be informative as to blood flow and the distribution of radioactive substances in the body.

Drawbacks to conventional PET and SPECT technologies are described below.

Attenuation

The influence of attenuation is a problem that impairs both PET and SPECT imaging. Attenuation is the result of the interaction between gamma rays (originated by electron-positron annihilation at a location in the subject's body) and electrons in another location of the subject's body. The attenuation interaction causes a gamma ray to lose a fraction or all of its energy due to phenomena known as Compton scattering and photoelectric absorption, respectively. As a consequence, attenuation causes PET and SPECT imaging apparatus to detect none or only a fraction of the original radioactive signal produced by the gamma rays, and may therefore lead to an incorrect estimate of the distribution of radioactive material in the body.

Some PET and SPECT imaging scanners have means of correcting for non-uniform attenuation. These scanners employ transmission scanning, in which gamma-rays or x-rays are transmitted from an emission source and through the patient or body part, to an opposing detector having a scintillator that is sensitive to gamma and/or x-rays, for example. The emission source that generates the gamma rays may be a radioisotope (e.g., sodium-22). Alternatively, for example, x-rays may be generated by a rotating anode source struck by an electron beam. The x-rays are absorbed by a scintillator, which then emits light. A photosensor transforms light emitted by the scintillator into electrical signals, which are converted by a computer into a transmission image. The transmission image provides anatomical information about the patient or object by indicating the electron density of the patient or object, which is informative as to the amount of attenuation caused by different structures of the patient or object. Attenuation scans have been implemented through the use of attenuation sources such as rotating radioactive rods or sleeves filled with gamma-emitting radioactivity that reside within the bore of the PET or SPECT detector, or from x-rays generated by an x-ray tube.

As mentioned above, the information furnished by the transmission image is potentially useful in the correction of attenuation affecting the emission image. In typical attenuation-correction procedures the PET or SPECT imaging scan is performed at a different time than the attenuation scan. The staggering of emission and transmission image scans is deemed necessary to avoid confusion between, on the one hand, gamma radiation generated within the body due to electron-positron annihilations caused by a radiotracer and, on the other hand, gamma radiation directed into and through the body for transmission scanning purposes.

Attenuation scans acquired by conventional apparatus and methods have proven problematic in the correction of attenuation effects on an emission image. PET scanners that employ rotating radioactive rods or a beta-detector-and-source assembly to generate an attenuation map have limited spatial resolution and count density. These limitations typically result in the generation of an anatomic image that is inferior to the images generated by rotating x-ray tubes. Furthermore, the rotating sources do not acquire a complete sampling of the attenuation of the body part at all times, because the rotating sources only have a limited number of views of the body part at any instance.

Additionally, in cases where the body part is in rapid motion, or where instruments or objects near the body part are in rapid motion, it can be difficult to correlate or "register" an attenuation transmission scan image of the body part with the emission image when the two sets of images are collected at different detection periods, that is, non-contemporaneously. For example, the non-contemporaneous acquisition of emission and transmission scan images occurs in the case of a PET/CT scanner where the CT images are collected from a CT scanner with a separate bore from the PET scanner. If the motion of the body part under examination is regular and repeatable, it may be possible to generate emission images and attenuation maps that correspond to the same cardiac or breathing cycle ("gated images"), and thus are better candidates for registration. Efforts have been made to develop software for correcting these non-contemporaneous, misaligned images by taking advantage of the regularity of breathing and cardiac motion. However, problems may arise with software correction of the misaligned images when the subject exhibits or is prone to various irregularities, such as non-regular breathing or cardiac dysrhythmias, in which body motions are not regularly repeated. Such irregularities may result in emission and transmission images that capture images of the body part, e.g., heart or diaphragm, in different positions that cannot be correctly registered with one another without resulting in the production of artifacts.

Scintillation Crystals

In commercial clinical whole-body PET scanners, the photosensors are typically photomultipliers, and each scintillator is viewed by multiple photomultipliers. In an alternative arrangement found in animal PET scanners and certain high-resolution clinical PET scanners, several photomultiplier anodes are housed in a single vacuum package (e.g., multi-anode position-sensitive photomultipliers). In this alternative arrangement, each photomultiplier anode typically views more than one scintillator. Typically, the scintillators are arranged as pillars in a "block" of multiple scintillator units. The scintillator block is coupled to a fixed number of photomultipliers, as described, for example, in U.S. Pat. No. 5,453,623 by Wong et al. The scintillator block design and "quadrant-sharing" arrangement of Wong is implemented in order to reduce fabrication costs for PET scanners. The photomultipliers of the PET scanners are expensive, and the quadrant sharing of photomultipliers lowers expense. Additionally, the Wong patent proposes that its quadrant-sharing arrangement reduces the amount of "dead" time experienced by each light detector following the detection of a gamma ray.

However, the scintillator block design imposes constraints on the member components. Specifically, because the overall block must be able to accommodate high photon flux rates in PET applications, it is the general view that the component scintillators in the block must have short decay times. If the scintillator components of this conventional block design were to have relatively longer decay times, the electrical signals generated by the photosensors that are in the block would "pile-up" or accumulate with one another before the scintillator signal could fully decay. As a consequence, the photosensors would be unable to distinguish individual gamma-ray detection events from one another, and the block effectively would be paralyzed during high rates of gamma-ray emission.

To avoid this paralysis predicament with respect to the scintillator block design, the PET industry has developed and used scintillators with short (i.e., less than 30 nanoseconds) decay times for photomultiplier applications. Examples of fast scintillators with short decay times include lutetium orthosilicate (LSO). Fast scintillators tend to be fabricated using a single-crystal growth process, as described in Czochralski, "Growth of Rare-Earth Orthosilicates ($Ln_2SiO_5$)", Brandle et al., Journal of Crystal Growth 79 (1986) pp. 308-315. Single crystalline scintillator materials are relatively expensive, especially compared to sintered scintillator materials.

PET scanner designs containing meta-arrays of photosensors individually coupled to individual, single-crystal scintillators with rapid decay times (e.g., lutetium orthosilicate, LSO) have also been proposed, as described in the publication by Pichler et al, "Performance Test of an LSO-APD Detector in a 7-T MRI Scanner for Simultaneous PET/MRI", in the 2006 issue of the Journal of Nuclear Medicine Vol. 47 No. 4 Pages 639-647. The rapid decay scintillators have been in these PET scanners presumably for the same reasons described above, e.g., to avoid the "paralysis predicament."

It is possible to fabricate scintillation crystals using a much less expensive sintering process described in, for example, the publication entitled "Cerium-doped lutetium aluminum garnet optically transparent ceramics fabricated by a sol-gel process," by Xue-Jian Liu et al., in J. Mater. Res. Vol. 21, No. 6, June 2006, pages 1519-1525. Lutetium aluminum garnet ("LuAG") has been described by some designers of PET scanners as a poor scintillator due to its long decay time (i.e, 2 microseconds), and has been derided as a contaminant in the preparation of other scintillators with shorter decay times, for example, as characterized in "LuAlO3:Ce-a high density, high speed scintillator for gamma detection", by Moses et al, IEEE Transactions on Nuclear Science, Volume 42, Issue 4, August 1995, pages 275-279. Sintered scintillator crystals have note been used in PET scanner devices, in part because the arrangement of either multiple scintillators viewed by a photosensor or a scintillator viewed by multiple photosensors imposes the requirement of shorter decay times than have been produced with sintered crystals.

Photosensors

Important considerations in the selection of photosensors include:

(a) Physical size: the amount of lead shielding needed to shield a photosensor/scintillator combination from extraneous sources of radiation is generally proportional to the volume of the photosensor. As a result, large photosensors require more shielding, which adds to overall cost and size of the medical device.

(b) Fabrication costs: photosensor cost represents a significant fraction of the expense associated with the medical device, and therefore is desirably minimized.

(c) Bias voltage: a low bias voltage is important, especially for interventional devices (e.g., intra-operative cameras), in order to reduce the possibility of electric shock to a patient.

(d) Gain: high gain is preferable in order to reduce the cost of amplification electronics, and to yield high signal-to-noise ratios.

(e) Linearity, energy resolution, and dynamic range: provide accurate measurements of the gamma-ray energy absorbed by the scintillator. High accuracy measurements permit discrimination between gamma-rays that have been scattered within a patient's body and gamma-rays that have not been scattered within the patient's body. The scattered gamma-rays provide less reliable information about the distribution of gamma-ray sources in the patient's body than the unscattered gamma-rays.

(f) Rise and decay times: short decay (recovery) times are important in order to reduce pulse pile-up high gamma-ray environments, such as in cardiac scans with short-lived radio-isotopes (e.g., Rb-82). Short rise times help to accurately measure the arrival time of the gamma-ray at the detector, which is of particular interest in PET scanner operations, where locations of gamma ray emissions are determined by the coincident detection of gamma rays by a pair of detectors.

(g) Dark current: signals generated without photon absorption having taken place are known as the "dark current", which is typically attributable to defects in or thermal variations experienced by the photosensor. Dark current is best kept at a minimum in order to yield high signal-to-noise ratio.

Many conventional photomultipliers and the related hybrid photon detector (HPD) technology have the advantages of high gain (one million or more), good linearity, and low dark current, but the disadvantages of large size, high voltage, sensitivity to ambient magnetic fields, and high expense. Large-area avalanche photodiodes (LAAPD) can offer linear amplification with wide dynamic ranges, but at fairly low gain (e.g., 100). This low gain results in poor signal-to-noise ratio.

An avalanche photodiode ("APD") may operate in a high-gain breakdown mode by increasing the bias voltage. Certain devices called single-photon avalanche detectors ("SPAD") take advantage of this high-gain operational mode to detect and register single photons of light. However, operation of the SPAD in breakdown mode results in loss of linearity for events in which multiple light photons are absorbed, because the current produced by the breakdown discharge is independent of the number of photons absorbed. Because of this loss of linearity, in breakdown mode the discharges produced due to dark current may be indistinguishable from discharges due to absorbed photons.

The publication of Golovin and Saveliev, entitled "Novel type of avalanche photodiode with Geiger mode operation," Nuclear Instruments and Methods in Physics Research" 518 (2004) 560-564 discloses an avalanche photosensor with Geiger mode of operation, referred to as a silicon photomultiplier. The silicon photomultiplier is described as a plurality of avalanche diodes (also referred to as micro-cells) on a single substrate with a common quenching mechanism (resistive layer) and a common electrode. An absorbed photon entering the micro-cell generates an electron-hole pair. Due to a reverse bias that is applied to the micro-cell, a drifting electron can generate a large number of electron-hole pairs via an avalanche process, resulting in break down of the micro-cell. The resistive layer is provided over the $n^+$-p-$\pi$-$p^+$ avalanche structure of the micro-cell for the purpose of quenching the avalanche process in the micro-cell.

Breakdown-mode micro-cell detection of an event is non-linear and hence does not give intensity information. The breakdown of a micro-cell due to the coincident absorption of photons produces a pulse that is indistinguishable from the output pulse produced by a thermally generated electron or hole, known as dark rate pulses (which for high rates can also be considered equivalent to a dark current). Such dark rate events represent false signals that desirably are minimized. The resistive layer provided over the $n^+$-p-$\pi$-$p^+$ avalanche structure of the microcell produces a localized collection of charge and reduction in the electric field at areas corresponding to crystal structure defects, thereby suppressing the ability of a dark charge to initiate an avalanche at those areas.

A drawback to the use of the resistive layer or other type of resistive and quenching elements over radiation-sensitive areas is that the resistive element attenuates and thereby reduces detection of certain frequencies of light, especially UV light, thereby limiting the efficiency of the photosensor.

SUMMARY OF THE INVENTION

A first aspect of the invention provides a camera sub-module for providing tomographic imaging of radiation emissions generated internally by a body, the camera sub-module comprising a radiation-emitting layer having a radioactive source for emitting transmission emissions, and at least one radiation-detection layer for contemporaneously detecting and permitting differentiation between the transmission emissions and emissions generated internal to an imaged body administered with a positron-emitting radiotracer.

A second aspect of the invention provides an imaging apparatus comprising a first camera sub-module, and a second camera sub-module constructed and arranged relative to the first camera sub-module to permit contemporaneously detection of and differentiation between transmission emissions and internally-generated emissions.

A third aspect of the invention provides a method of providing a tomographic image of a body, comprising administering a positron-emitting radiotracer to a body for producing positrons which interact with the body to generate emissions internally, directing transmission emissions through the body, and contemporaneously detecting and differentiating between the transmission emissions and the internally-generated emissions.

A fourth aspect of the invention provides a quantum detector array, comprising a substrate, one or more avalanche sensor elements situated on the substrate, the avalanche sensor elements having radiation-sensitive areas for detecting radiation from a radiation-emission source, and quenching elements electrically interconnected to the avalanche sensor elements. The quenching elements are positioned at least partially outside of the radiation-sensitive areas to leave at least portions of the radiation-sensitive areas available to detect the radiation without obstruction from the quenching elements. Related aspects involve meta-arrays of the quantum detector arrays of the fourth aspect, and methods for detecting radiation with the quantum detector array and meta-array.

A fifth aspect of the invention provides a quantum detector-readout system, comprising a quantum detector array, comprising a substrate, avalanche sensor elements situated on the substrate, the avalanche sensor elements having radiation-sensitive areas for detecting radiation from a radiation-emission source, and quenching elements electrically interconnected to the avalanche sensor elements. The quenching elements are positioned at least partially outside of the radiation-sensitive areas to leave at least portions of the radiation-sensitive areas available to detect the radiation without obstruction from the quenching elements. The system further comprises a read-out system electrically interconnected to the quantum detector array for processing signals received from the quantum detector array. Related aspects involve meta-array readout systems comprising a plurality of the quantum detector-readout systems of the fifth aspect, and methods for detecting radiation with the quantum detector array readout system and the meta-array readout system.

A sixth aspect of the invention provides a quantum detector-readout system, comprising a quantum detector array comprising a substrate and avalanche sensor elements situated on the substrate, the avalanche sensor elements having radiation-sensitive areas for detecting radiation from a radiation-emission source, and a discriminator electrically interconnected to the quantum detector array for distinguishing spontaneous independent breakdowns of the avalanche sensor detectors from coincident breakdowns of a plurality of the avalanche sensor elements. Related aspects involve meta-array readout systems comprising a plurality of the quantum detector-readout systems of the sixth aspect, and methods for detecting radiation with the quantum detector array readout system and the meta-array readout system.

A seventh aspect of the invention provides a quantum detector-readout system, comprising a quantum detector array comprising a substrate and avalanche sensor elements situated on the substrate, the avalanche sensor elements having radiation-sensitive areas for detecting radiation from a radiation-emission source and generating signals, and a discriminator electrically interconnected to the quantum detector array for receiving the signals from the quantum detector array and associating timing information with the signals. Related aspects involve meta-array readout systems comprising a plurality of the quantum detector-readout systems of the seventh aspect, and methods for detecting radiation with the quantum detector array readout system and the meta-array readout system.

An eighth aspect of the invention provides a quantum detector-readout system, comprising a radiation-emission source, a quantum detector array, and an analog-to-digital converter. The quantum detector array comprises a substrate and avalanche sensor elements situated on the substrate, the avalanche sensor elements having radiation-sensitive areas for detecting radiation from a radiation-emission source and for generating analog signals, wherein the analog signals are generated by spontaneous independent breakdowns of the avalanche sensor elements or coincident breakdowns of the plurality of the avalanche sensor elements. The analog-to-digital converter converts the analog signals to digital signals having a value representative of the number of the avalanche sensor elements undergoing coincident breakdown. Related aspects involve meta-array readout systems comprising a plurality of the quantum detector-readout systems of the eighth aspect, and methods for detecting radiation with the quantum detector array readout system and the meta-array readout system.

A ninth aspect of the invention provides a quantum detector system or meta-array, comprising plurality of radiation-sensitive scintillators for emitting photons in response to detected radiation, the scintillators comprising multiple crystals sintered together, and a meta-array of solid-state, quantum photosensors. Each of the photosensors is operatively coupled to and paired with an associated one of the scintillators so that each one of the solid-state, quantum photosensors receives photons from only the associated one of the scintillators with which the solid-state, quantum photosensor is paired, and so that the photons emitted from each one of the scintillators are received only by the associated one of the solid-state, quantum photosensors with which the scintillator is paired.

A tenth aspect of the invention provides a method of detecting radiation, comprising detecting radiation with a plurality of radiation-sensitive scintillators and emitting photons in response to detected radiation, the scintillators comprising multiple crystals sintered together, operatively coupling and pairing each scintillator of the plurality of radiation-sensitive scintillators with an associated solid-state, quantum photosensor of a meta-array of solid-state, quantum photosensors, and transmitting the photons from the scintillator only to the associated solid-state, quantum photosensor with which the scintillator is paired.

An eleventh aspect of the invention provides an imaging apparatus for providing tomographic imaging of a body, comprising a manipulable platform, at least one camera sub-module mounted on the manipulable platform, and at least one position sensor for identifying the positions of the camera sub-module. The camera sub-module comprises one or more radiation-sensitive scintillators for emitting photons in response to detected radiation, and one or more solid-state, quantum photosensors.

A twelfth aspect of the invention provides a quantum detector-readout system, featuring a radiation-emission source, a quantum detector array, and a discriminator. The quantum detector array comprises a substrate and avalanche sensor elements situated on the substrate. The avalanche sensor elements have radiation-sensitive areas for detecting radiation from a radiation-emission source and generating signals. The discriminator is electrically interconnected to the quantum detector array for distinguishing spontaneous independent breakdowns of the avalanche sensor detectors from coincident breakdowns of a plurality of the avalanche sensor elements. Related aspects involve meta-array readout systems comprising a plurality of the quantum detector-readout systems of the twelfth aspect, and methods for detecting radiation with the quantum detector array readout system and the meta-array readout system.

A thirteenth aspect of the invention provides a quantum detector-readout system, featuring a radiation-emission source, a quantum detector array, and a discriminator. The quantum detector array comprises a substrate and avalanche sensor elements situated on the substrate. The avalanche sensor elements have radiation-sensitive areas for detecting radiation from a radiation-emission source and generating signals. The discriminator is electrically interconnected to the quantum detector array for receiving the signals from the quantum detector array and associating timing information with the signals. Related aspects involve meta-array readout systems comprising a plurality of the quantum detector-readout systems of the thirteenth aspect, and methods for detecting radiation with the quantum detector array readout system and the meta-array readout system.

A fourteenth aspect of the invention provides a quantum detector-readout system, featuring a radiation-emission source, a quantum detector array, and an analog-to-digital converter. The quantum detector array comprises a substrate and avalanche sensor elements situated on the substrate. The avalanche sensor elements have radiation-sensitive areas for detecting radiation from a radiation-emission source and for generating analog signals, wherein the analog signals are generated by spontaneous independent breakdowns of the avalanche sensor elements or coincident breakdowns of the plurality of the avalanche sensor elements. The analog-to-digital converter is electrically interconnected to the quantum detector array for converting the analog signals to digital signals having a value representative of the number of the avalanche sensor elements undergoing coincident breakdown. Related aspects involve meta-array readout systems comprising a plurality of the quantum detector-readout systems of the fourteenth aspect, and methods for detecting radiation with the quantum detector array readout system and the meta-array readout system.

Additional aspects of the invention are described below in connection with the detailed description and attached figures, and include, for example, the sub-modules, imaging apparatus, systems, arrays, meta-arrays, photosensors, and methods described below.

BRIEF DESCRIPTION OF THE DRAWINGS

The accompanying drawings are incorporated in and constitute a part of the specification. The drawings, together with the general description given above and the detailed description of the preferred embodiments and methods given below, serve to explain the principles of the invention. In such drawings.

Figure 1:
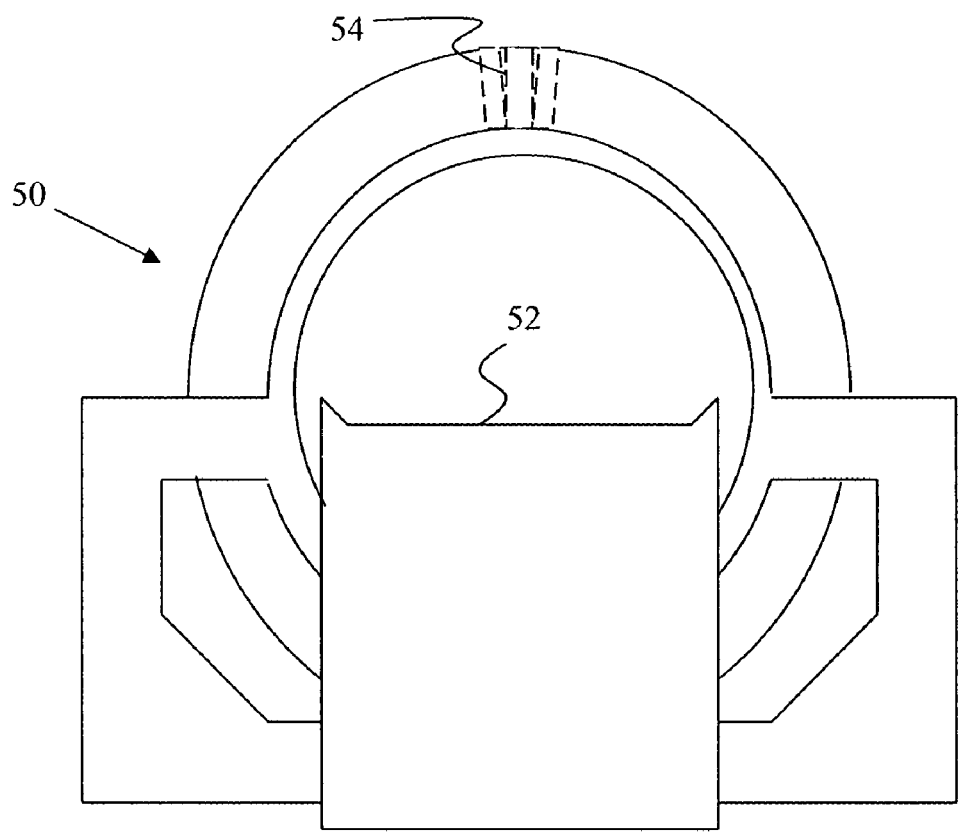
FIG. 1 is a front elevational view of a PET scanner.

DETAILED DESCRIPTION OF PREFERRED EMBODIMENTS AND PREFERRED METHODS OF THE INVENTION

Reference will now be made in detail to the presently preferred embodiments and methods of the invention as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the preferred embodiments and methods. The invention according to its various aspects is particularly pointed out and distinctly claimed in the attached claims read in view of this specification, and appropriate equivalents.

PET Scanner

Embodiments of the invention described herein are especially useful for providing tomographic imaging of a body which has been administered a positron-emitting radiotracer, which emits positrons that interact with internal parts or structures of the body via electron-positron annihilations to create internally-generated annihilation emissions. Examples of internal parts or structures that may be imaged include various organs, such as the liver or heart. For the purposes of clarity and brevity, gamma rays created by annihilations between electrons of the body or body part and positrons emitted by the radiotracer internal to the body or body part are denoted "internally generated annihilation emissions." It should be understood the embodiments described herein may be employed to image body parts and structures that have been excised or otherwise removed from the body, e.g., in vitro or ex vivo), such as in the case of a biopsy, and it should be further understood that emissions generated by interaction of radiotracer positrons and such body parts and structures removed from the body are likewise referred to herein as internally-generated annihilation emissions.

A PET scanner, generally designated by reference numeral 50, is illustrated in FIG. 1. PET scanner 50 includes a bed 52 on which the patient is positioned during the scanning procedure. An annular configuration of units or banks 54 surrounds bed 52. Although shown as a circular ring, it should be understood that the annular configuration may possess a polygonal shape, such as a hexagon. Bed 52 may be movable relative to banks or units 54 to permit movement of the patient through the annular configuration. As referred to herein, relative movement may mean movement of bed 52 while retaining banks 54 stationary, movement of banks 54 while retaining bed 52 stationary, or movement of both bed 52 and banks 54.

Figure 2:
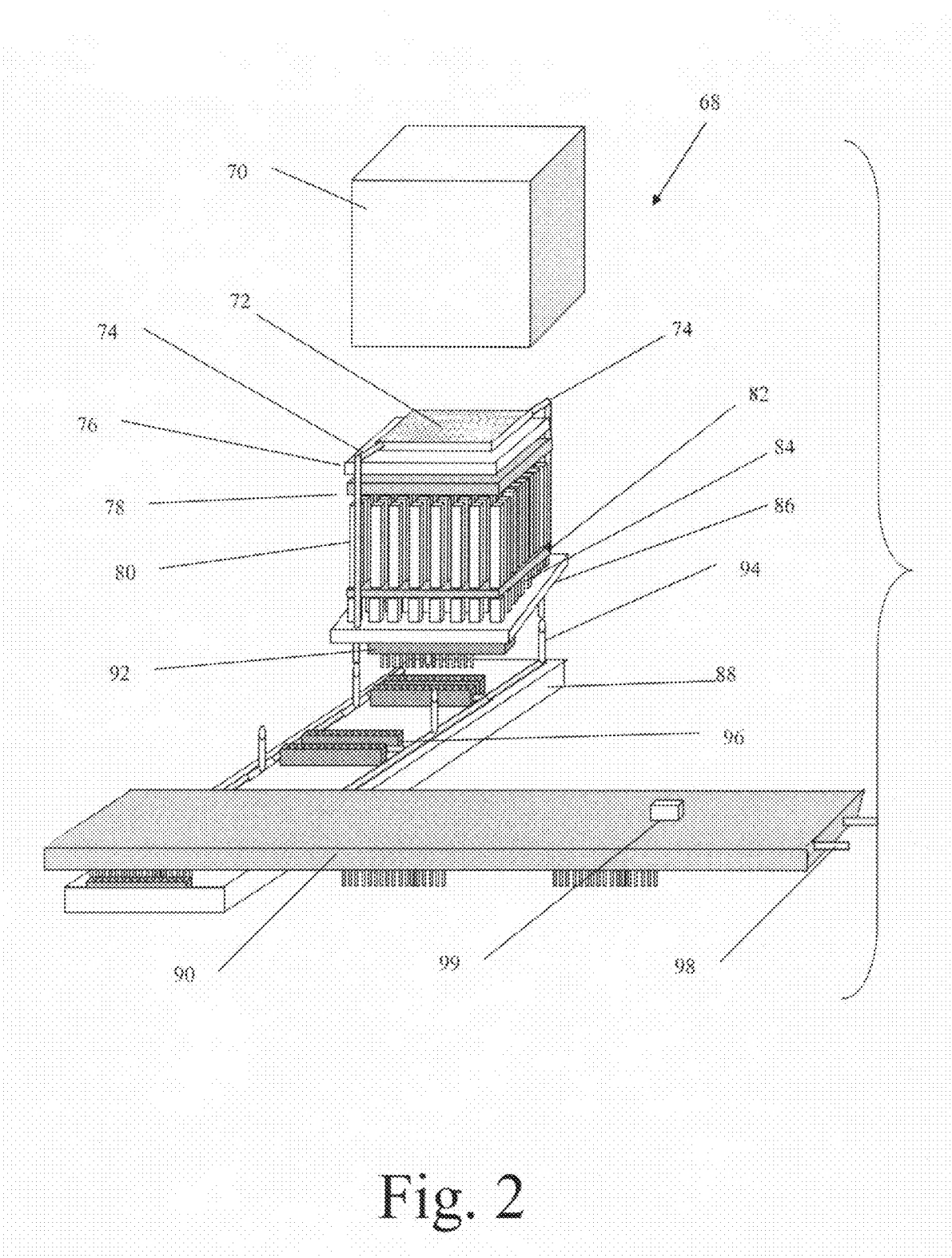
FIG. 2 is a schematic, perspective view of a camera sub-module according to an embodiment of the invention.
Figure 3A:
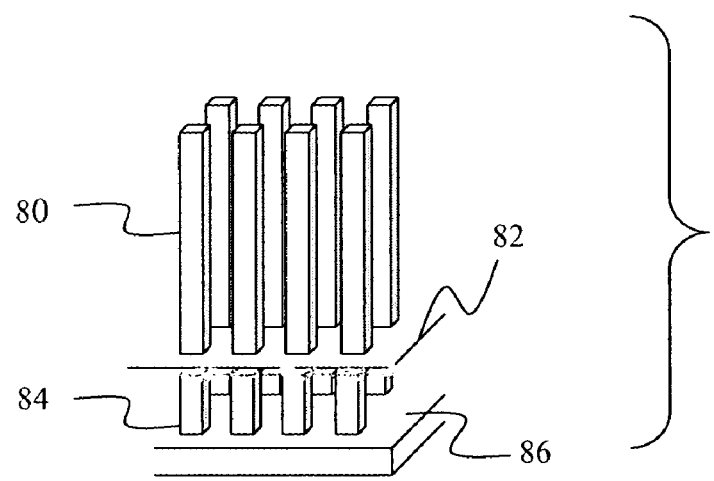
FIGS. 3A and 3B are a perspective top fragmented view and a bottom fragmented view of a meta-array of photosensors and scintillators of the sub-module of FIG. 2, including a wiring diagram.

Each bank 54 possesses one or more sub-modules, generally designated by reference numeral 68 in FIG. 2. As best shown in FIG. 3A, sub-module 68 includes a meta-array of scintillators 80 and photosensors 84, described in greater detail below. Banks 54 of the annular configuration are arranged in PET scanner 50 so that scintillators 80 are positioned radially inward relative to photosensors 84.

Referring back to FIG. 3, sub-module 68 includes a cover 70 that prevents the transmission of beta radiation and light, while admitting low and high energy gamma-rays and/or x-rays. Such a cover could be made of plastic or thin aluminum.

Under cover 70, camera sub-module 68 includes a radiation-emitting layer 72 of radiation-emitting substance for emitting one or more forms of radiation. The radiation from layer 72 is transmitted through the body, and as a result is referred to herein as transmission emissions. For example, the radiation-emitting substance may comprise a beta-gamma emitter such as Xe-133. Layer 72 may be constructed as a container for holding a gaseous or liquid radioactive substance. Alternatively, layer 72 may be a solid radioactive substance such as an epoxy solution of radioactive elements. In the illustrated embodiment, radiation-emitting layer 72 can be further described as a thin-walled hollow container possessing a chamber and made of a transmissive material, such as a plastic. The chamber of layer 72 is filled with at least one radioactive material that preferably emits multiple radiations, for example Xe-133 which emits 80 keV gamma rays and 100 keV (average energy) beta rays. The wall of layer 72 is sufficiently thin to allow gamma radiation together with beta radiation (or other tagging radiation) to transmit therethrough. Optionally, the selected material of layer 72 may constitute a scintillating material. Although depicted as a planar source, layer 72 may be a linear or point source.

Conduits, such as hollow tubing 74, are provided for delivering the radiation-emitting substance to layer 72 and for removing the radiation-emitting substance from layer 72. In this manner, the radiation-emitting substance can be replenished (e.g., on a weekly basis), and/or substance may be withdrawn in the event that the seal of layer 72 is compromised. For example, conduits 74 can be used to charge or discharge-Xe-133 as needed or desired. The Xe-133 can be discharged, for example, into a sump containing activated charcoal, as is commonly found in a nuclear medicine facility for performing ventilation-perfusion scans, and as studied in a published article entitled "Adsorption and Desorption of Noble Gases on Activated Charcoal: I. Xe-133 Studies in a Monolayer and Packed Bed" published in Health Physics, Vol. 59, pp. 383-392, October 1990 and authored by Scarpitta et al.

The gamma rays emitted from radiation-emitting layer 72 may be low energy (e.g., 50 keV, similar to x-rays) or high energy (e.g., energy levels comparable to gamma rays emitted from electron-positron annihilations). In accordance with an embodiment of the invention, radiation-emitting layer 72 simultaneously emits at least one additional type of radiation, also referred to herein as a marker or tagging emission, such as beta and/or alpha emissions, as discussed in greater detail below. For example, radiation-emitting layer 72 may comprise a planar, linear, or point source containing positron-emitting radioisotopes such as germanium-68, which emits a positron and two gamma-rays upon decay. As an alternative embodiment, radiation-emitting layer 72 may contain a radiation emitter that does not emit positrons, but instead emits simultaneous or nearly simultaneous multiple radiations in the form of gamma rays, with or without "markers" (for example, Cd-109, Co-57, Eu-152, Ta-182, Th-228, Tm-170, Xe-127, Xe-133, or Yb-169). One may select a low-energy emitter that simultaneously produces a low-energy gamma ray and a beta ray (e.g., Xe-133), for example. Alternatively, the positron-emitting radioisotope may have a "third" gamma-ray (e.g., as in Na-22) which when detected would suggest that the event arose from radiation-emitting layer 72. Auger electrons may be used as well as the marker, in radioactive materials that decay via electron capture, such as Tl-201, as described in "Beta camera low activity tumor imaging" published in Acta Oncol. 1993;32(7-8):869-72 and authored by Ljunggren et al. It is also possible for layer 72 to contain multiple emitting substances that collectively emit two, three, or more different types of emissions, e.g., positrons, gamma-rays, and beta-rays.

A thin (or first) radiation-detecting layer 76 is positioned adjacent to radiation-emitting layer 72. Thin radiation-detecting layer 76 is primarily sensitive to the marker or tagging rays (e.g., layer 76 has high stopping power to the beta rays emitted from layer 72), and has lesser sensitivity (e.g., low stopping power) with respect to high energy gamma rays (e.g., from electron-positron annihilation). For example, in an embodiment thin radiation-detecting layer 76 can detect beta rays emitted by the Xe-133 of radiation-emitting layer 72, and can also detect the low-energy gamma rays emitted by Xe-133 from a different sub-module, and still also can detect Compton interactions (e.g., from annihilation photons that deposited some, but not all, of their energy in radiation-detecting layer 76). The use of beta-gamma coincidences to detect Xe-133 is described in articles such as "Digital coincidence counting (DCC) and its use in the corrections for out-of-channel gamma events in 4 pi beta-gamma coincidence counting", published in Appl Radiat Isot. January-February 2002; 56(1-2):205-10, and authored by Keightle et al.

Thicker radiation-detecting layer 80, which is relatively sensitive (high stopping power) with respect to gamma rays, is illustrated as segmented into scintillating needles or columns with coatings on the four longest sides in order to optimize light collection. Alternatively, the scintillator may be in the form of solid or semi-segmented blocks. Preferably the scintillator (or other radiation detector) material selected as layer 80 has sufficient stopping power to absorb gamma-rays via photoelectric interaction.

Light guide 78 or an air gap is positioned behind thin radiation-detecting layer 76 to separate layers 76 and 80 from one another. Light guide 78 may have wavelength shifting properties, and may be structured in order to obtain high confidence measurements of the location where the scintillation occurred, as discussed in the article "GePEToS: A Geant4 Monte Carlo simulation package for Positron Emission Tomography", published in IEEE Transactions on Nuclear Science 52 (2005) and authored by Jan et al.

Thick radiation-detecting layer 80 is coupled to photosensors 84, which convert light from radiation-detecting layers 76 and 80 into analog electrical signals. Coupling may be accomplished via a coupling material 82 with wave-shifting properties. The interface or coupling material 82 between layer 80 and photosensors 84 may comprise air, transparent glue or grease, a wave-shifting material, a structured light-guide, or other material. Alternatively, coupling material 82 may be omitted, so that thick radiation detecting layer 80 and photosensors 84 are in direct end-to-end contact. Photosensors 84 may comprise, for example, high-gain avalanche photodiodes (also known as silicon photomultipliers). Exemplary high-gain avalanche photodiodes are described below with reference to FIGS. 9-12.

In the illustrated embodiment of FIG. 2, thin radiation-detecting layer 76 may be a scintillator, and thick radiation-detecting layer 80 may be made of a transparent or otherwise transmissive scintillator material to permit scintillating light from thin radiation-detecting layer 76 to be transmitted through transparent thick radiation detecting layer 80 to photosensors 84.

Resolving whether the light energy originated from thin radiation-detecting layer 76 or thick radiation detecting layer 80 may be accomplished by making layers 76 and 80 from materials with different decay times. That is, thin radiation-detecting layer 76 may be made of a material such as scintillating plastic whose scintillation characteristics can be differentiated by photosensors 84 from scintillation characteristics of thicker radiation detection layer 80 on the basis of decay time or other characteristics. Analysis of the electrical waveforms output by photosensors 84 can discriminate between slow and fast decay times. The discrimination is readily accomplished when the electrical waveform is digitized through a sampling analog-to-digital converter, and fitted with an exponential decay model. Alternatively the duration may be recorded to measure the time that the signal is above two thresholds (e.g., "time-over-threshold"). An example of a combination of scintillating materials (so-called "phoswich") is discussed in a report to the United States government under contract DE-FG02-04ER89121, entitled "Digital Pulse Shape Analysis with Phoswich Detectors to Simplify Coincidence Measurements of Radioactive Xenon" by Whennig et al. For example, thin radiation-detecting layer 76 of camera sub-module 68 may contain a thin scintillating material that produces more (or less) light per collected gamma ray than layer 80 and has a shorter (or longer) decay time (e.g., lanthanum bromide, or plastic scintillators) than the scintillating material of layer 80 (e.g., bismuth germanate, or lutetium orthosilicate).

Figure 4:
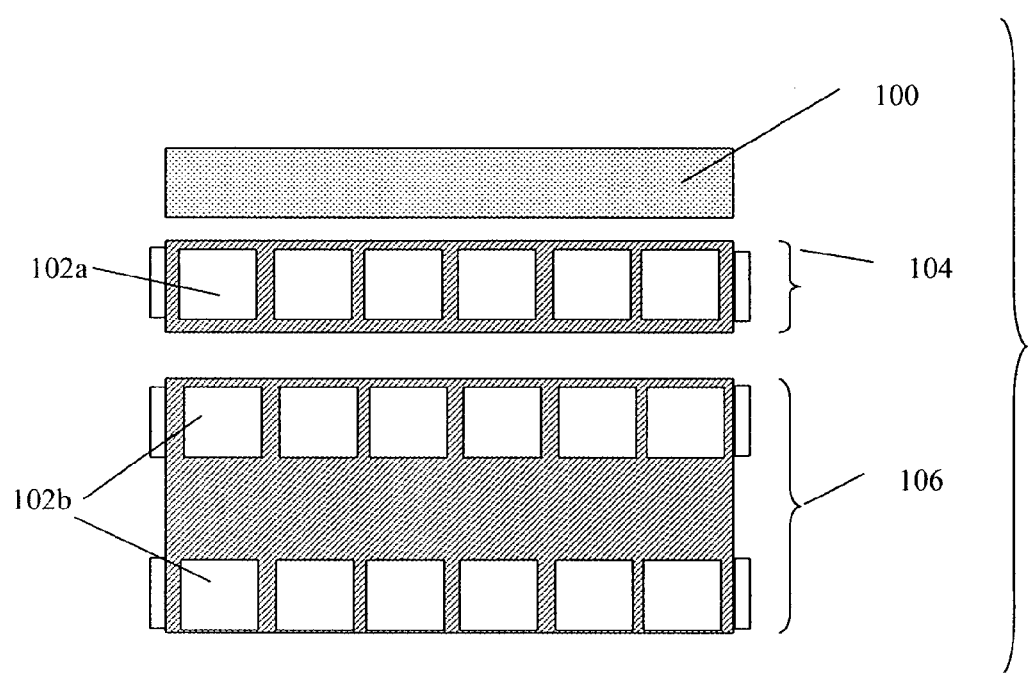
FIG. 4 is a schematic, sectional view of another embodiment in which respective radiation-detecting layers are surrounded by photosensor sets.

Alternative or complementary designs and methods for resolving whether the collection of energy has occurred in either thin detector layer 76 or thick detector layer 80 may be employed. For example, thin radiation-detecting layer 76 and/or thick layer 80 need not be a scintillator. Instead either or both of layers 76 and 80 may be solid-state detectors such as Silicon APD or PIN diode or CdTe or CdZnTe detectors in which direct conversion of the gamma or beta rays to electrical signals may occur. Another alternative embodiment shown in FIG. 4 includes a radiation-emitting layer 100, similar to radiation emitting layer 72 of FIG. 2. In FIG. 4, a first plurality of photosensors 102a is provided in proximity to and operatively coupled to thin radiation-detecting layer 104 (comparable to layer 76 of FIG. 2). A second plurality of photosensors 102b is provided in proximity to and operatively coupled to thick radiation-detecting layer 106 (comparable to layer 80 of FIG. 2). Light emitted by scintillator 104 is only detected by photosensors 102a, while light emitted by scintillator 106 is only detected by photosensors 102b. In the alternative embodiment of FIG. 4, it would not be necessary for one set of photosensors to discriminate between events detected in scintillators 104 and 106. The arrangement of FIG. 4 would be useful, for example, with extremely bright scintillators such as sodium iodide or lanthanum bromide. As still another method for resolving whether the collection of energy has occurred in either thin detector layer 76 or thick detector layer 80, the energy of both layers 76 and 80 of a sub-module 68 may be summed on an event-by-event basis. For example, if the total energy from both layers 76 and 80 is greater than 511 keV, corresponding to the energy of annihilation of a positron, then it may be assumed that a second gamma or beta ray added to the annihilation photon energy.

Photosensors 84 can be electrically connected together in a resistive chain or chains, for example, extending in the x- and y-directions independently. A general discussion regarding the use of silicon photomultipliers ("SiPM") devices in PET is provided in Moehrs et al, "Small-Animal PET Design Using SiPMs and Anger Logic with Intrinsic DOI" given at the 2004 IEEE Nuclear Science Symposium and Medical Imaging Conference in Rome, Italy in October 2004, and submitted as a publication to the IEEE Transactions on Nuclear Sciences.

Figure 3B:
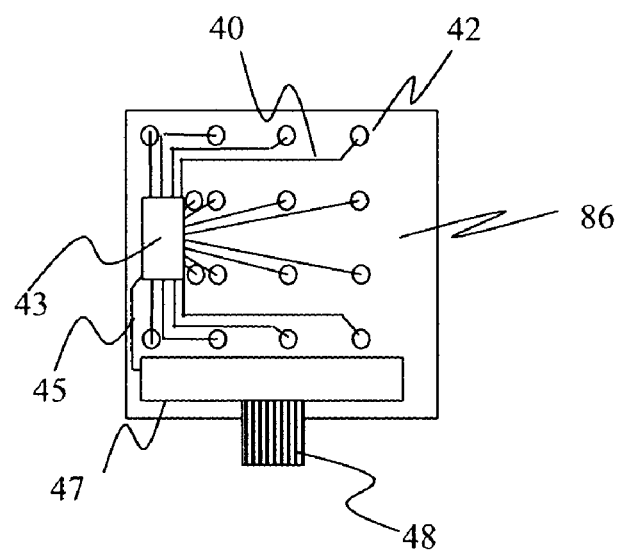

Photosensors 84 are connected to electronic components in base layer 86 (also referred to herein as an electrical component layer) capable of converting the analog electrical signals into digital signals. As generally shown in FIG. 3B and described in greater detail below, base layer 86 may include electronic components, such as resistive or time-delay elements, cooling elements (e.g., Peltier active cooling, heat sink), analog-to-digital converters, buffers, trigger circuitry, constant fraction and/or comparator discrimination circuitry, timestamp circuitry (possibly with a field-programmable gate array). Photosensors 84 may be connected to each other via resistors in the base layer 86, so as to reduce the number of inputs to the electronic circuit ("resistive readout"). Alternatively, photosensors 84 may be connected to each other via time-delay elements, to reduce the number of inputs to the electronic circuit ("time-delay readout"). As another example, base layer 86 may read out each photosensor 84 individually. The electronic circuit in base layer 86 may include one or more analog-to-digital converters ("ADC") or time-to-digital converters ("TDC") in conjunction with a waveform analyzer and a circuit capable of determining the time of the event ("timestamp"), the location within the camera sub-module (e.g., which amount of energy was deposited in which section of which scintillator layer), and the energy of the event. The photosensors may have a pre-amplifier, or may have sufficient signal strength that a preamplifier is not needed. The photosensors and entire PET scanner may be placed in a magnetic field.

First connector board 88 shown in FIG. 2 includes electrical bus connections 92 to deliver and receive digital electrical signals via sockets 96 that interface with connectors 92 of sub-module 68. Second connector board 90 carries the bus information from first connector board 88 to a computer for processing and analysis. Second connector board 90 also supplies calibration signals and power to first connector board 88 and to the electrical components. Preferably, the bus receives digital information concerning time, energy, location, and layer of the event, as digitized by electrical component layer 86. Alternatively, the buses can have analog-to-digital or time-to-digital converters that receive analog information from electrical component layer 86.

Connector boards 88 and 90 may also carry Xe-133 via conduits (e.g., tubing) 98, which connect with conduits (e.g., tubing) 94 connected to conduits 74 in order to charge and discharge the Xe-133 or other emission material to and from thin radiation-emitting layer 72. First connector board 88 preferably is removable to enhance serviceability of sub-module 68. First and second connector boards 88 and 90 can be assembled into rings or flat panels or other PET CT configurations. Connector boards 88 and 90 are meant to be representative and illustrative of various means of connecting the photosensors to the remainder of the system, and may be replaced in part or wholly by other elements, for example wireless transmitters, cables, etc.

Figure 18:
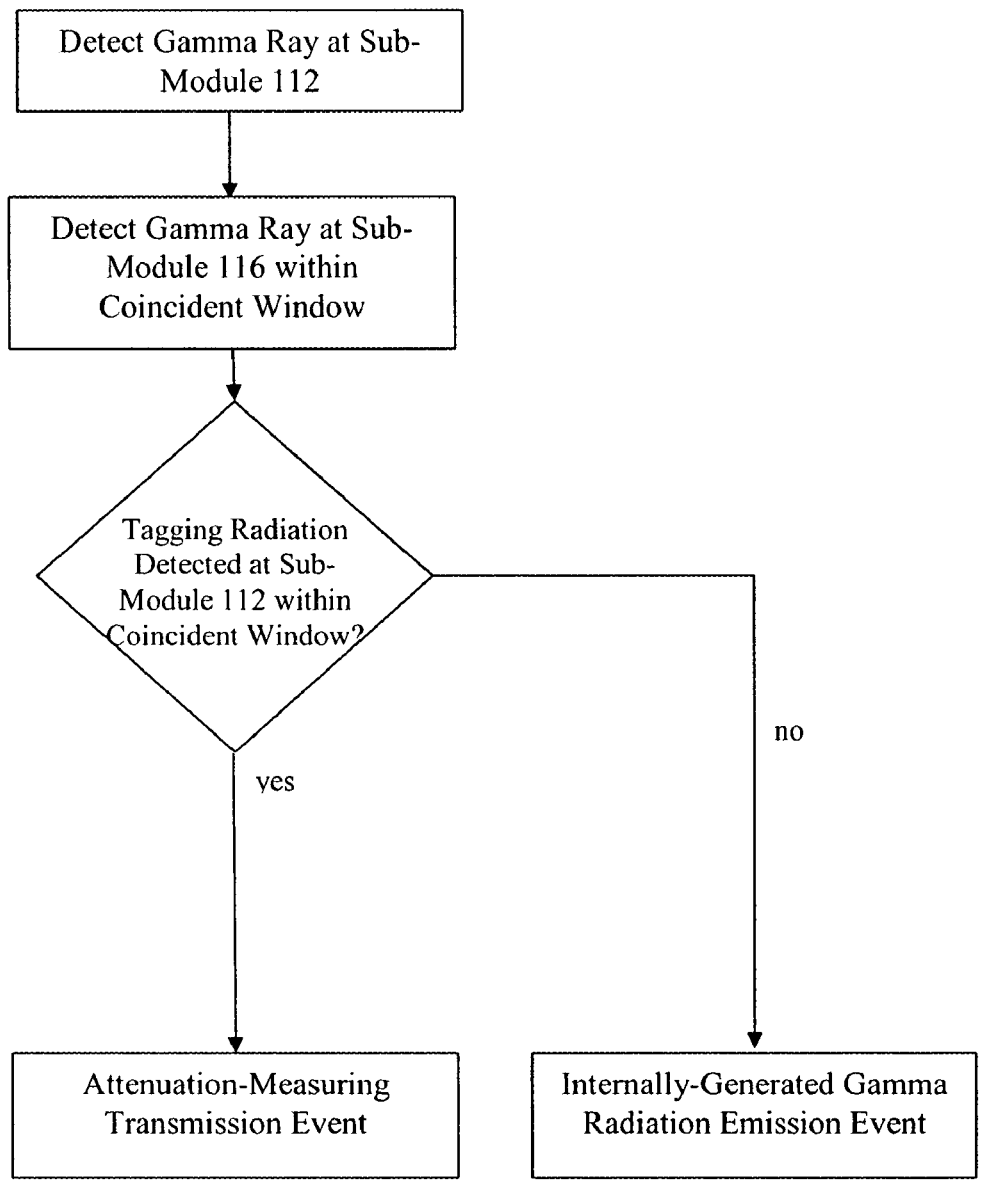
FIG. 18 is a flowchart of tagging methodology for concurrently reading and interpreting image and attenuation emissions.

Position detectors or sensors 99 are shown in FIG. 2 mounted on board 90, but may be secured to any components of sub-module 68 or other structures of the camera bank 54. Position detectors 99 provide additional flexibility in configuration and enhance the mobility of the scanner 50. Position sensors have been incorporated into many devices that are in wide use in the entertainment industry, including gloves for virtual reality applications (e.g., CyberGlove), as described in U.S. Pat. No. 4,988,981. The use of position sensors 99 can be integrated into the data collection and reconstruction algorithm in a manner similar to the article "Flexible geometries for hand-held PET and SPECT cameras," published in the 2001 IEEE Nuclear Science Symposium Conference Record, Volume 2, 4-10 Nov. 2001 Page(s): 1133-1136, by Weinberg et al. or a variation thereof, e.g., in which the positions of sub-modules are known with respect to one another. Alternatively, the projection of gamma-rays emitted from radiation-emitting layer 72 onto other panels may be used to determine relative positions of the panels relative to one another In order to accurately accomplish the contemporaneous detection of transmission emissions from layer 72 and radioactive internally-generated annihilation emissions, it is useful to "tag" either the radioactive internally-generated annihilation emissions or the transmission emissions generated by layer 72, so that the emissions of one source may be distinguished from the emissions of the other source. Tagging can be performed, for example, using the following approach represented in the flowchart of FIG. 18.

The radiation generated by electron-positron annihilations originating from the radiotracer imbued in the body or body part differs in decay scheme from the radiation emitted from layer 72. The source of transmission radiation, e.g., layer 72, is selected from among those elements with a decay scheme that includes both a first form of radiation, and a second form of radiation that is emitted at essentially the same time as the first form of radiation. Preferably, the first form of radiation comprises gamma rays. The second form of radiation is the "tag" or marker and may comprise, for example, alpha rays, beta rays, x-rays, and/or Auger electrons.

Detection of the second form of radiation (e.g., beta-ray, x-ray, or other marker) at layer 76 acts to tag the event, in particular the detection of a gamma ray at a second sub-module within a coincident window, as an attenuation-measuring transmission event. For example, referring to FIG. 5, a beta-gamma transmission emission 113 is emitted from emission layer, e.g., 112a, causing a beta ray to be detected at thin detection layer 112b of sub-module 112, and a first gamma ray to likewise be detected at either thin detection layer 112b and/or thick detection layer 112c, depending on the energy of the gamma ray and the stopping power of layer 112b. Within a coincident window (e.g., ten nanoseconds from the time of detection of an event in layer 112b), a second gamma ray will be detected at thin and/or thick detection layers 116b, 116c of opposite sub-module 116.

The detection of the beta and gamma rays within a narrow coincident timing window) implies that the detected gamma-ray event arose from thin-radiation-emitting layer 112a, as opposed to internally-generated gamma radiation arising from electron-positron interaction in the body part imbued with positron-emitting radiotracer. This implication is surmised because beta-radiation from the positron-emitting radiotracer would be internally absorbed by body 128 and would not be detectable by sub-module 116. On the other hand, gamma radiation generated by the body's internal radiotracer, e.g., at 126, would not necessarily be detected within an applicable coincidence window of beta radiation, thus distinguishing, on the one hand, the internally-generated gamma radiation arising from interaction between body 128 and positrons of the radiotracer from, on the other hand, the gamma radiation emanating from layer 112a and transmitted through body 128. The coincident timing window can be determined by the size of the apparatus bore (see FIG. 1) and the speed of the radiation. For example, gamma rays travel at a velocity of about $3 \times 10^{10}$ cm/second. Travel across a 60 cm bore would take the gamma ray approximately 2 nanoseconds. Thus, the coincident window may be set, for example, at about 2 nanoseconds, for the above-described apparatus having a 60 cm bore. The coincident window may be adjusted accordingly, for example, for different dimensioned apparatus and other design and operational features.

Because the emission image information is collected contemporaneously with the attenuation image information, the sets of information are more easily registered with one another. Accordingly, the attenuation map and/or emission image correction information corresponding to the position of the patient's body is a more accurate representation of the electron density of the body, and hence the attenuation effect of the body, than would be the case if the patient had separate attenuation and emission scans (as is the case for the current generation of PET/CT scanners). Further, the collection of emission image and attenuation information can be accomplished with very high efficiency, and the collected information can be used to provide an attenuation map for purposes of calibrating the PET image and/or for providing anatomic information that may provide diagnostic confidence to the scanner operator.

It should be understood that the embodiment depicted in FIG. 2 may be altered and manipulated into various modified and alternative arrangements, non-exhaustive examples of which are discussed below and/or shown in the drawings. In the embodiments depicted in FIG. 5, for example, radiation-emitting layers of the various sub-modules 110, 112 (i.e., layer 112a), 114, and 116 (i.e., layer 116a) are formed as a unitary chamber or layer contiguous with one another and shared by each of the sub-modules 110, 112, 114, 116 (rather than providing a discrete radiation-emitting layer for each of the sub-modules). Ports 118 permit input and removal of radioactive substance. The radiation-emitting layer of this alternative embodiment may comprise, for example, a film of plastic containing positron-emitting radioisotopes.

As another possible modification, thick radiation-detecting layer 80 may be segmented into a group of separate layers. It is also within the scope of the invention to reverse the order of layers, interchange layers, merge layers, split layers, omit layers, or add additional layers. Further, the thickness of layers 76 and 80 relative to one another may vary, e.g., layer 76 may be thicker than layer 80, or the layer thicknesses may be equal to one another.

According to another embodiment, thin radiation-detecting layer 76 and thick radiation-detecting 80 layers are combined into a single thick radiation-detecting layer. According to this alternative embodiment, the combined radiation-detecting layer is capable of depth-of-interaction detection, permitting determination of the location along the thickness of the detecting layer that energy is absorbed. Deeper penetration of radiation within the detecting layer is generally indicative of high energy radiation, such as gamma rays emitted from radiotracer at 126, whereas lesser penetration is generally indicative of lower energy radiation, such as beta rays emitted at 113. Useful materials for the radiation-detection layer of this embodiment include lutetium orthosilicate (LSO) scintillators. Depth of penetration may be measured by placing photosensors at various depths of the scintillator, for example, as the photosensors 102b are shown placed at different depths in FIG. 4. The proportion of light detected by the photosensors at varying depths of the scintillator is related to the depth of penetration of the gamma ray in the scintillator.

Photosensors 84 and their associated readout electronics may be constructed compactly, to reduce expense and facilitate arrangement of photosensors 84 into flexible configurations, such as the free-hand scanner (e.g., glove) embodiment described below. For example, electronics layer 86 may be combined with photosensors 84, for example, by placing some or all of the digitizing electronic elements (e.g., analog-to-digital converters, comparators) on the same chip or in the same physical package as the photosensors 84.

Figure 6:
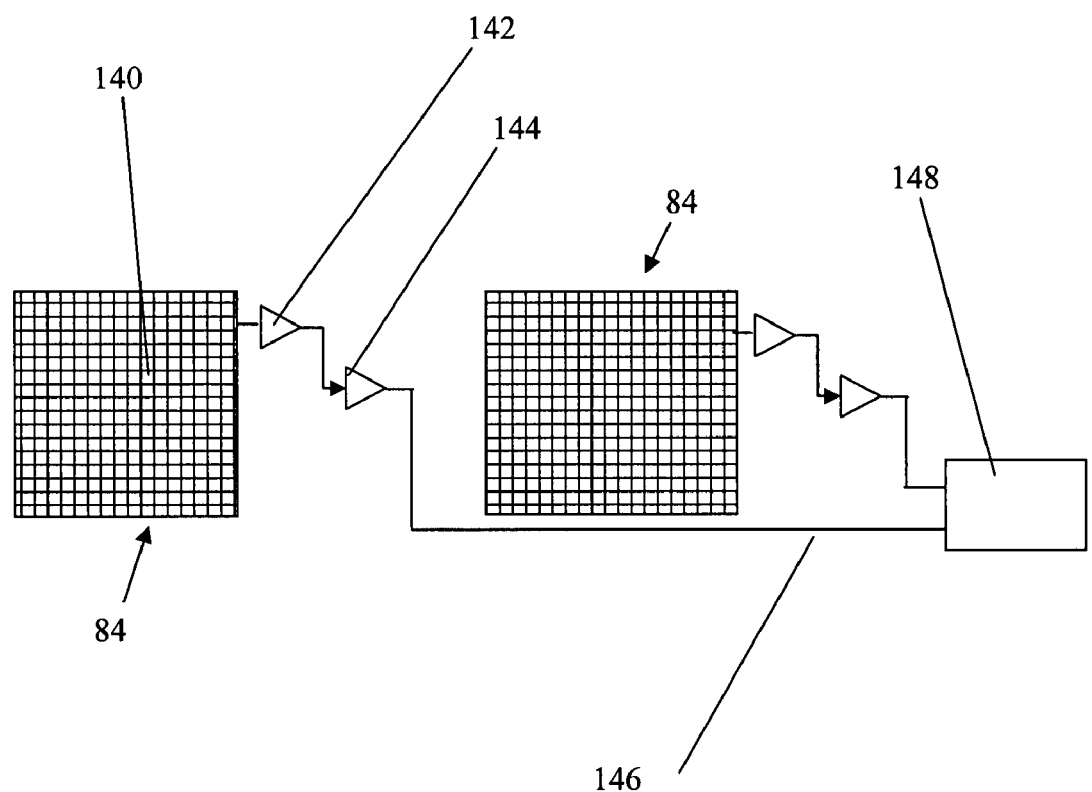
FIG. 6 is a schematic of an embodiment of photosensors that may reside within a sub-module, and associated readout electronics can be configured in a compact manner.

FIG. 6 illustrates photosensors 84 establishing a radiation sensitive region of individual avalanche photodiode tiles 140 (or micro-pixels). Each tile 140 is sensitive to at least a single photon of light generated by a scintillator layer, such as layer 80 above. In the preferred embodiment, each small domain, e.g., tile 140, is isolated from its adjacent domains, such as by a trench, as described in the publication by V. Saveliev and V. Golovin, "Silicon avalanche photodiodes on the base of metal-resistor-semiconductor (MRS) structures", published in Nuclear Instruments and Methods in Physics Research A 442 pp. 223-229 (2000). A timing and trigger circuit (also referred to as a comparator) 142 provides readout electronics so that if more than one micro-pixel is activated, analog-to-digital conversion is triggered (e.g., by analog-to-digital converter 144). Because each micro-pixel is triggered by a single quantum of scintillator light, comparator 142 (or other threshold circuit, e.g., a constant fraction discriminator) examines the summed signal from all the micro-pixels to determine if the summed signal represents a minimum number of (e.g., at least two) photons. If this threshold is achieved, the comparator triggers digitization of the summed signal. The resulting digital signal is transferred, for example, by a trace or set of traces 146, and stored, for example, in a buffer and/or summing element 148 or otherwise processed, for example, in the same chip or other chips. If the threshold is not achieved, the signal is dismissed as dark current_and not digitized, as discussed further below. In an alternative embodiment, each micro-pixel is examined by a comparator or other threshold circuit, and the aggregation of data from each micro-pixel is entered into a counter to form a digital signal which can be stored in a buffer or otherwise processed in the same chip or other chips. In an alternative embodiment, the comparator(s) 142 and buffers and/or summing elements 148 for each set of small domains are fabricated on the same wafer as the small domains, in physical locations corresponding to the gaps between photosensors 84.

As another alternative embodiment, some or all of the digital and analog elements of base layer 86 may be fabricated or disposed on one or more wafers and bonded together with one or more wafers containing the photosensor or meta-array of photosensors 84, similar to the arrangement discussed below in reference to FIG. 17. Sections of these wafers may be arranged in a single package. For example, the bridge-bonding approach method described in a publication by B F Aull et al in "Geiger-Mode Avalanche Photodiodes for Three-Dimensional Imaging", Lincoln Laboratory Journal 13(2) pp. 335-350 (2002) could be used to fabricate this alternative embodiment. Using the bridge-bonding approach, the readout CMOS chip is adhered, such as with an epoxy, face-to-face with the corresponding APD array, and to a handle wafer (with the APD's substrate side up). The APD substrate is removed from the APD/readout/handle sandwich and replaced by a shallow p+ implant, followed by a laser anneal and metallization, to replace the electrical contact formerly provided by the substrate. Vias (e.g., traces that connect one side of the substrate to the other) are then etched in between the APDs and metal bridges patterned within the vias to connect each APD with the corresponding readout circuit. In an alternative embodiment, the readout CMOS chip is bonded to the other side of the APD array chip (i.e., the epitaxial side instead of the substrate side). In another alternative embodiment, the APD layer may be connected to the comparator layer in a three-dimensional structure (e.g., fabricated by 3-D CMOS). With such a three-dimensional structure, the sum of micro-pixels may be digitized, or comparators may be placed below each micro-pixel in order to form a direct digital signal that can be counted.

These are just a few of the modifications and alternative arrangements that can be implemented to the sub-module device of the invention. Other modifications and alternative arrangements would be within the purview of a skilled artisan having reference to this disclosure.

Figure 5:
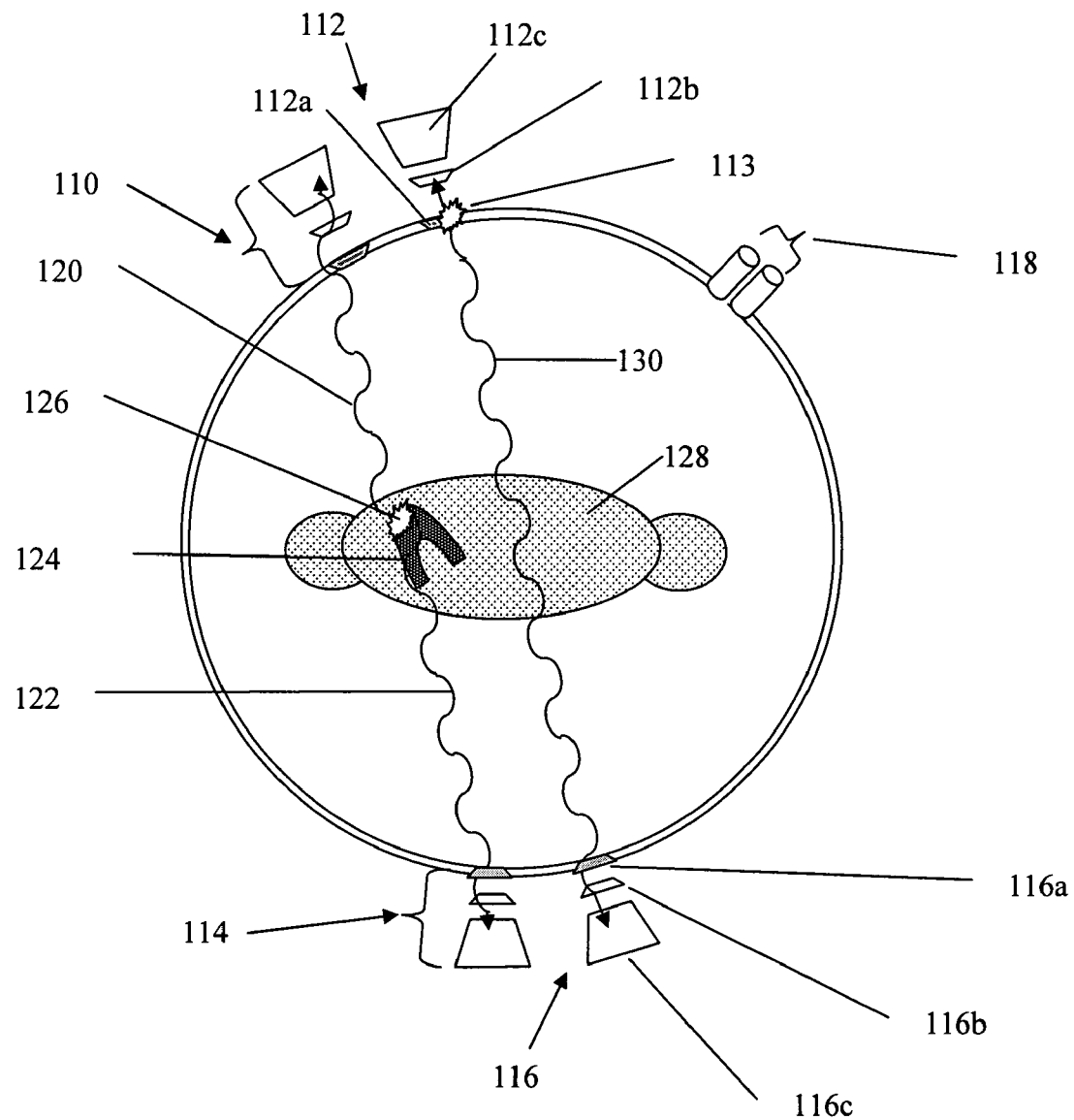
FIG. 5 is a schematic, partially sectioned view of a PET CT scanner possessing a plurality of the camera sub-modules of FIG. 3.

The following is an example of an apparatus and method for performing a scan of a particular radiotracer (Rb-82) injected into a human body. It should be understood that the depicted apparatus may be used in conjunction with other radiotracers. FIG. 5 shows an embodiment of a PET CT device, featuring a ring of multiple camera sub-modules 110, 112, 114, 116. Only a few sub-modules are shown. Typically, multiple sub-modules are arranged annularly in a ring around a human subject's body 128. The heart wall (myocardium) of the human subject is shown in cross section 124. The myocardium 124 is imbued with a positron-emitting radiotracer such as Rb-82, which decays by positron emission 126, giving off two 511-keV gamma rays (120 and 122) in opposite directions. It should be understood that the invention may be practiced for the imaging of other or multiple body parts. Further, the apparatus and method may be practiced on subjects other than humans, such as in the case of veterinarian applications. The invention also may be practiced with respect to objects and instruments, especially objects and instruments implanted or otherwise introduced into a subject or body part. Such instruments include, for example, biopsy tools, therapeutic and diagnostic interventional tools, probes (e.g., cryotherapy probes), RF heating coil or other ablative instruments, minimally invasive technology, etc.

In the embodiment depicted in FIG. 5, each sub-module (e.g., 110, 112, 114, 116) includes a thin radiation-emitting layer, e.g., 112a (corresponding to layer 72 of FIG. 2), a thin radiation-detecting layer, e.g., 112b (corresponding to layer 76 of FIG. 2), and a thick radiation-detecting layer, e.g., 112c (corresponding to layer 80 of FIG. 2). The electronics layer and light-guide layers are present in the actual device design, but for simplicity are not shown in FIG. 5. Radiation-emitting layers, e.g., 112a, 116a, etc. may be connected together to establish a continuous common chamber partially or completely surrounding subject 128. The chamber of thin radiation-emitting layer 112a is charged with a dose of Xe-133 or other radiation-emitting materials via port 118.

Beta and gamma rays emitted by Xe-133 of thin radiation-emitting layer 112a of sub-module 112 are detected in thin radiation-detecting layer 112b and thick radiation-detecting layer 112c, respectively, of the same sub-module 112. The 80 keV gamma ray 130 emitted simultaneously with beta radiation from the Xe-133 of sub-module 112 traverses body 128, and is detected in thick radiation-detecting layer 116c of sub-module 116, which is substantially opposed to sub-module 112. Electrical signals from photosensors that read out thin radiation-detecting layer 112b of sub-module 112 and thick radiation-detecting layer 116c of sub-module 116 are interpreted by a computer to show that both events occurred within a designated coincidence timing window, and are therefore determined to have arisen from the beta-gamma decay of the Xe-133. Because gamma ray 130 in many cases traverses human subject 128 to reach a sub-module on the opposite side of the ring, the detection of a multiplicity of such events permits construction of an attenuation map of the human subject. This attenuation map represents an attenuation image of the human subject 128 (i.e., an x-ray computed tomographic, or "CT" image), and can also be used to quantitatively correct for the effect of attenuation in the emission image whose formation will be discussed below. In addition to providing attenuation information about a human subject, attenuation information is provided about instrumentation which may reside within the bore of the PET CT scanner, thereby adding information that may be useful during therapeutic or diagnostic interventions.

Xe-133 can emit 50 keV photons as well as 80 keV photons, due to K-shell x-rays, as discussed in the article "High Sensitivity Detection of Xenon Isotopes via Beta-Gamma Coincidence Counting", a report given at the 21$^{st}$ Seismic Research Symposium and sponsored by the U.S. Department of Energy under contract number DE-AC06-76RLO 1830, and authored by Bowyer et al. By having the computer calculate the amount of deposited energy of the gamma ray or x-ray, it is possible to construct an attenuation map. Such a map would be helpful in differentiating types of anatomic structures from one another, such as calcifications or iodinated injected contrast material in vessels.

The collection of emission data from myocardium 124 can be shown by examining the detection of 511 keV gamma rays 120 and 122. FIG. 5 illustrates the detection of gamma rays 120 and 122 by the thick radiation-detecting layers of sub-modules 110 and 114, respectively. Photosensors of sub-modules 110 and 114 convert light emitted from the radiation-detecting layers into electrical signals, which are interpreted by a computer to show that both events occurred substantially simultaneously, and are therefore determined to have arisen from the annihilation 126 of a positron in body 128. The combination of a multiplicity of such events permits construction of a map of the concentration of radiotracer Rb-82 in the human body (i.e., an emission map), subject to attenuation by the human body. The emission map is commonly referred to as the positron emission tomography ("PET") scan, and when corrected by the attenuation map provides a quantitative measurement of the distribution of Rb-82 in the human body.

Although not shown in the figures, the exposure of operators of the PET CT apparatus to gamma-rays and x-rays given off by the radiation-emitting layer may be reduced by placing appropriate shielding materials in the bore and bore entry of the PET CT apparatus. Shielding is described in the article "Evaluation of a Neck-Shield for Use During Neurological Studies with a Whole-Body PET Scanner", published in IEEE Trans. Nucl. Sci. 48:4 1512-1517 (2001) and authored by Thompson et al.

One advantage of certain embodiments of the invention is that the emission data and attenuation data may be obtained in the same position and overlapping acquisition periods, so that the emission and attenuation images may be correctly registered, regardless of motion of the patient or body parts, such as the rhythmic motion of a heart wall. This advantage is particularly applicable and significant when examining cardiac disease, in which attenuation images of small anatomic structures (e.g., calcified coronary arteries) may be correlated with functional abnormalities visible on PET (e.g., perfusion measurements). With very good spatial resolution, it is possible to collect information about the anatomy of coronary arteries from the early phase of the Rb-82 injection, and compare that information with myocardial perfusion data collected in a later phase of the Rb-82 scan.

Another advantage of certain embodiments of the invention is the efficient collection of attenuation information through the three-dimensional acquisition reconstruction geometry (e.g., volumetric reconstruction). With the high stopping power of the radiation detectors described above, and the high collection efficiency, it may be possible to employ a lower overall radiation dose to a patient from the CT component of the PET CT scan, compared to conventional scanning techniques.

It should be understood that while the illustrated embodiment of FIG. 5 depicts the sub-modules arranged to establish classical annular (i.e., ring-like) geometries of CT and PET imaging, other geometries may be practiced. For example, the camera sub-modules may be arrayed into two clam-shells which are separable from each other in order to make the device more portable. Other planar or curved detector arrangements are possible, with the detectors being either movable or stationary. Planar configuration of sub-modules may be used in approximation to a body part as in positron emission mammography. Alternatively, at least one sub-module may be internal to a body. The camera sub-modules can be placed within a magnetic field, for example in or near an MRI scanner, near or in a CT scanner, or in or near an ultrasound or other type of scanner. The use of radiation-emitting layers to collect attenuation information may be helpful in these geometries for anatomic-functional correlation and the detection and localization of interventional tools.

The attenuation and emission data collected by the camera sub-modules can be integrated with other physiological data (e.g., electrocardiographic or respiratory signals) in order to achieve gated scans and thereby improve spatial resolution and physiological significance.

The camera sub-modules can be assembled into a PET or SPECT scanner without attenuation correction or with attenuation correction (i.e., into a PET/CT or SPECT/CT scanner). The attenuation emissions may be used for purposes other than image correction, including preparation of a representative map of the electron density of the patient's body, or for multiple purposes.

Figure 7:
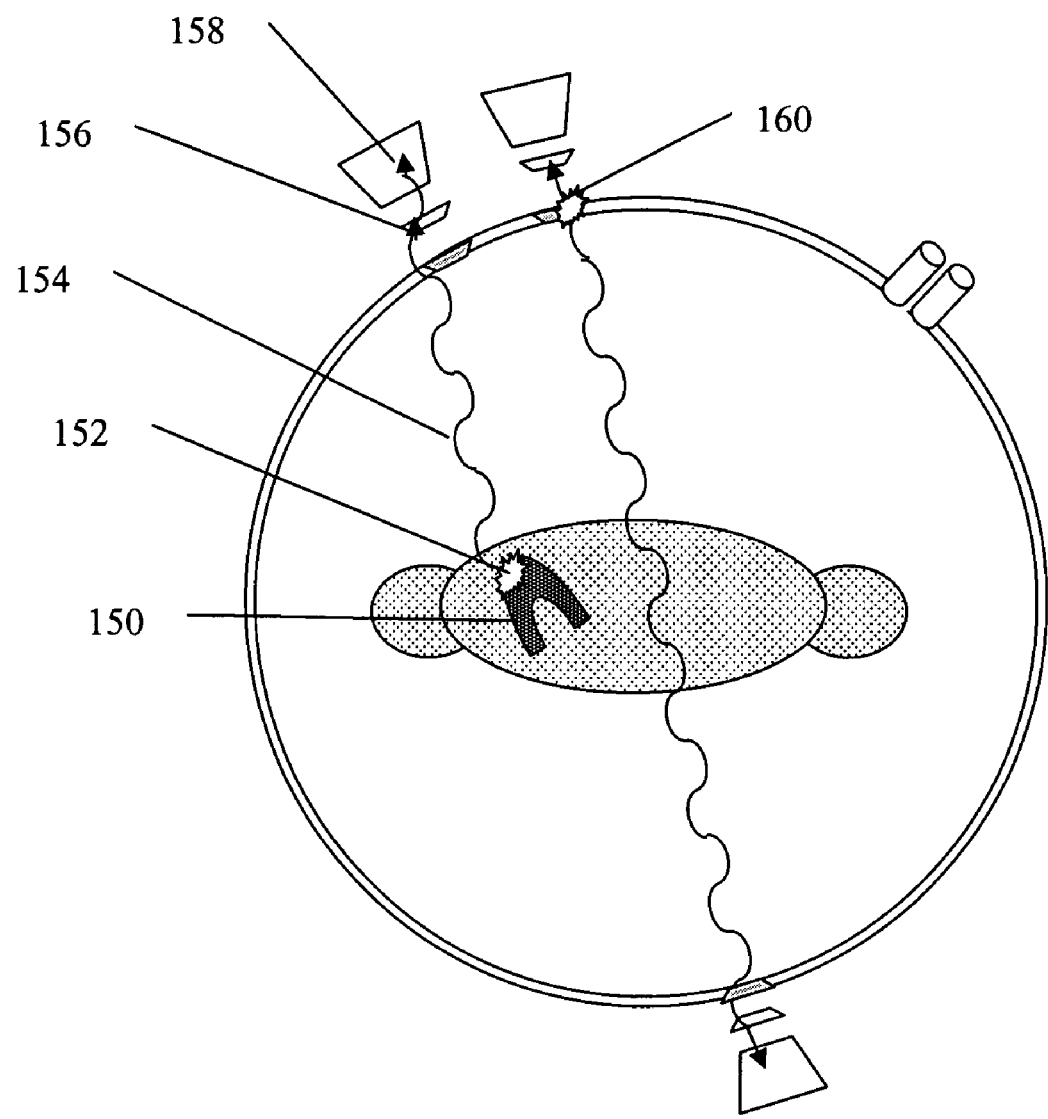
FIG. 7 is a schematic, partially sectioned view of an alternative embodiment in which the sub-modules can be used as a SPECT-CT device to detect gamma-rays from single-photon emitting radiotracers.

In the embodiment described above with respect to FIG. 5, positron-emitting radiotracers imbue body part 124. FIG. 7 illustrates an alternative embodiment in which body part 150 is imbued with single-photon emitting radiotracers such as Tc-99 m, or with positron emitters in which gamma-ray detection is accomplished from only one side of a body part. The gamma-decay 152 of such radiotracers leads to a gamma-ray 154, whose direction may be determined with the Compton camera mode of operation. The Compton camera mode of operation has been described in an article entitled "An electronically collimated gamma camera for single photon emission computed tomography. Part II: Image reconstruction and preliminary experimental measurements", published in 1983 Med. Phys. 10 (4) 428-435, and authored by Singh et al., the disclosure of which is incorporated herein by reference Generally, the Compton-camera operates as follows: Thin radiation-detecting layer 156 initially detects energy deposited from a Compton scattering of gamma ray 154. The residual energy of gamma ray 154 not completely absorbed by layer 156 is then detected in the nearby or adjacent thicker radiation-detecting layer 158. The locations on layers 156 and 158 at which the energy was detected may be used in a Compton-camera mode to assist in assigning a line-of-response defining the vector of the incident gamma ray.

The use of radiation detectors able to resolve very small amounts of energy deposition (e.g., quanta) allows for the detection and measurement of small angular deviations based on the deposit only small amounts of energy at layers 156 and 158. Computer processing of the events permits calculation of the angular deviation of the gamma-ray between the two layers in order to approximate the direction from which gamma-ray 154 originated. The algorithmic reconstruction of a combination of a multiplicity of such events allows for the generation of a map of the concentration of the single-photon radiotracer in the human body (i.e., an emission map), subject to attenuation by the human body. Qualitatively, the algorithm includes back projection of rays from the scattering medium towards the approximate direction of the source, and adding the angular deviation to each ray. A similar method is described in A Compton Scatter Camera for Spectral Imaging of 0.5 to 3.0 MeV Gamma Rays (PhD Dissertation). J B Martin. University of Michigan, 1994.

The emission map is commonly referred to as the single photon emission tomography ("SPECT") scan, and when corrected by the attenuation map (obtained from computer processing of the Xe-133 emissions 160) provides a semi-quantitative measurement of the distribution of the Tc-99 m in the human body. The source of gamma emission for this alternative embodiment may be determined, for example, by the detection (or absence) of a tagging beta ray at another detector within an appropriate coincident window. The gamma rays emitted from body part 150 would not have a coincident tagging beta ray, whereas gamma rays from the radiation-emitting layer (e.g., at 160) would be characterized by a tagging event within a coincident window. The collection of lines-of-response is used to reconstruct images.

High Mobility Platform

Figure 8:
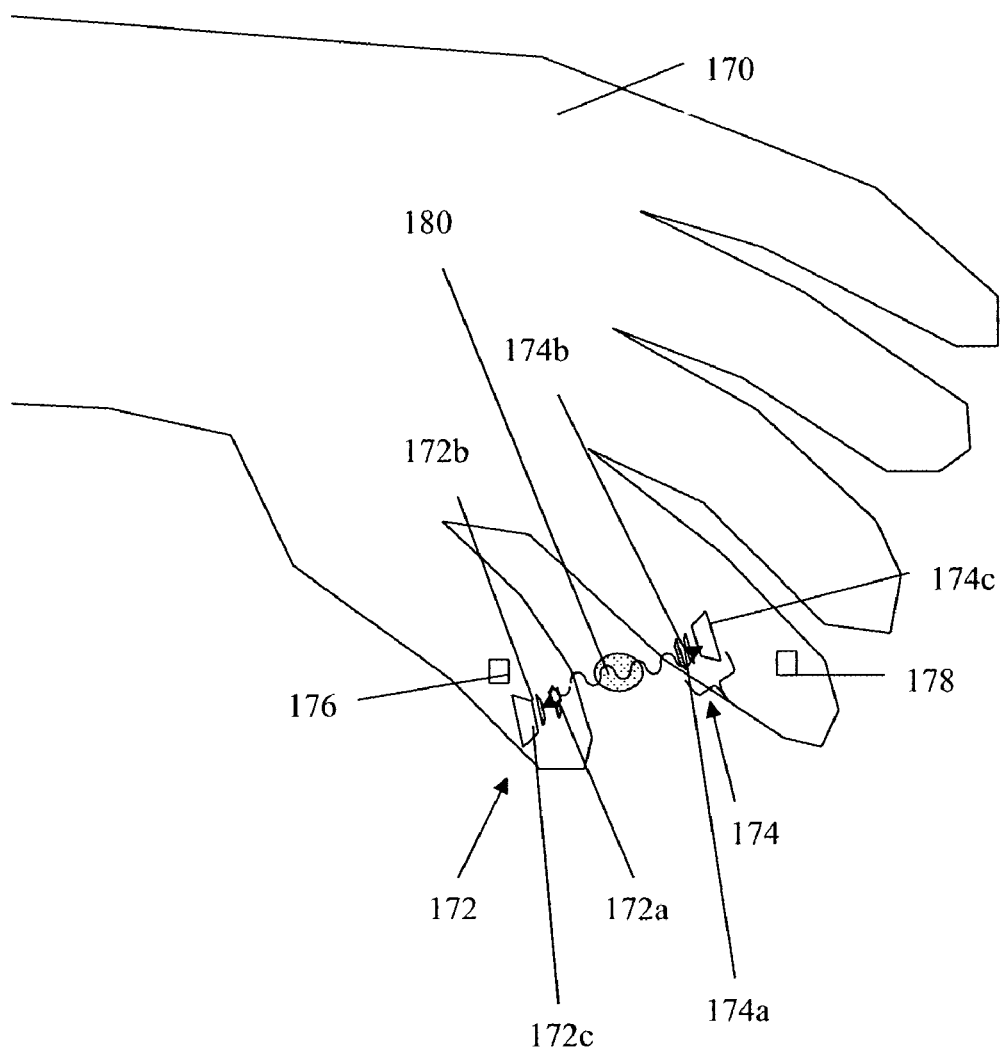
FIG. 8 is an embodiment of sub-modules, such as illustrated in FIG. 3, mounted in a glove or other free-hand device to detect gamma rays and x-rays.

FIG. 8 illustrates an embodiment of the invention in which position sensors (similar to reference numeral 99 described above) are placed on or within a glove 170 integrated with one or more detector sub-modules. Glove 170 includes a first camera sub-module 172 and a second camera sub-module 174. First camera sub-module 172 includes an emission layer 172a, a thin radiation-detecting layer 172b, a thick radiation-detecting layer 172c, and an associated first position detector 176. Second camera sub-module 174 includes an emission layer 174a, a thin radiation-detecting layer 174b, a thick radiation-detecting layer 174c, and an associated second position detector 178. Position sensors 176 and 178 serve to identify the location of detector sub-modules 172 and 174 with respect to one another. First and second sub-modules 172, 174 detect gamma-rays emanating from object 180 imbued with radioactive material, some of whose gamma rays are subtended by the fingers of glove 170. In the manner described above, an emission image may be generated based on gamma rays detected by sub-modules 172, 174. In another embodiment, operation of glove 170 may be performed with a single camera sub-module employing the Compton mode, such as described below in reference to FIG. 7.

Optionally, either or both of first and second detector sub-modules 172, 174 may include a radiation emitter layer (172a and 174a) for generating transmission radiation. The source used to generate the transmission radiation may be a radio-isotope, as in the above description utilizing Xe-133. Alternatively, a compact source of x-radiation may be used, such as a catheter with an x-ray source as in U.S. Pat. No. 6,475,168 by Pugsley et al. Thin radiation-detector layers 172b, 174b permit detection of transmission radiation from radiation emitter layers 172a, 174a for establishing an attenuation image and/or for correction of the emission image, as discussed in greater detail above. Thin shielding material may be placed between the source of radiation and the operator's fingers for safety purposes.

Various modifications may be made to the above-described embodiment. For example, glove 170 may be used to determine the internal structure of an object 180 that is not radioactive or imbued with radioactive material, by detecting radiation emitted by radiation emitting layers 172a, 174a in a manner as described above to provide an attenuation scan without an emission scan. The attenuation scanning capability of the devices and apparatus permit the free-hand manipulable detector device to serve as a portable CT scanner. It should be understood that this embodiment may be modified to employ platforms other than gloves, especially highly mobile platforms freely movable along random or unpredictable (e.g., not pre-set) paths to provide the platform operator with a high degree of flexibility with respect to freedom of motion. Alternatively, the operation of the detectors 172 and 174 may occur without the need for radiation-emitting elements 172a or 174a. As another alternative, radiation detectors 172b and 172c may operate in a Compton-detecting mode, as previously described.

Quantum Detector Array

An embodiment of a quantum detector array that may be employed as a photosensor 84 of camera sub-module 68 and the scanner 50 described above follows. It should be understood that the quantum detector array described below may be implemented with camera sub-modules and systems other than those described above, e.g., conventional sub-modules and scanners.

Figure 9:
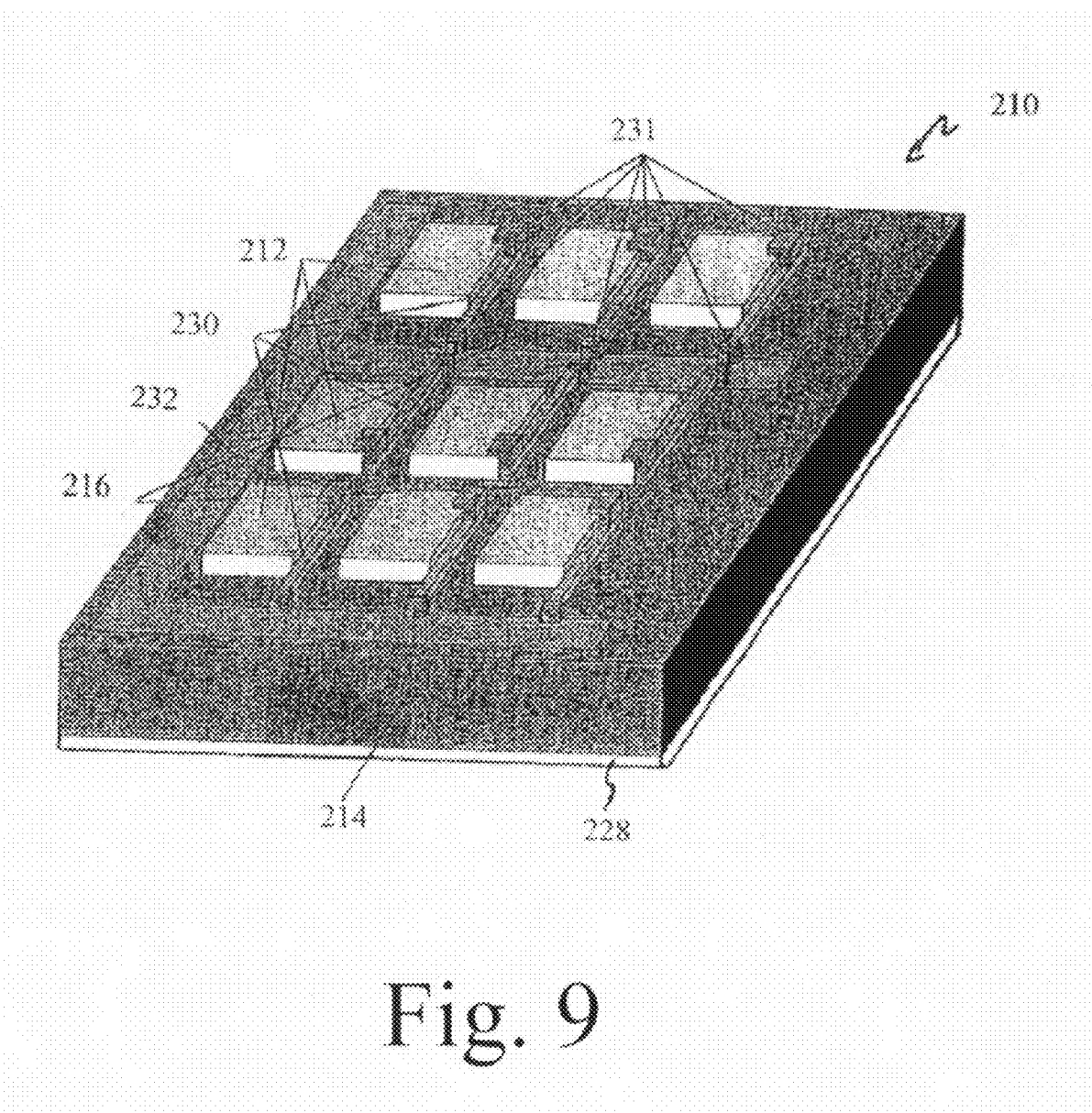
FIG. 9 is a perspective view of a quantum detector array according to an embodiment of the invention.

FIG. 9 is a perspective view of a photosensor comprising quantum detector array 210 according to a preferred embodiment of the invention. As shown in FIG. 9, quantum detector array 210 features sensor elements or tiles 212 and a common substrate 214, preferably made of silicon, although it should be understood that other semiconductor materials may be selected, such as gallium arsenide, germanium, gallium nitride, etc. Each sensor element 212 corresponds to a single micro-cell, e.g., tiles 140 depicted in FIG. 6.

Figure 10:
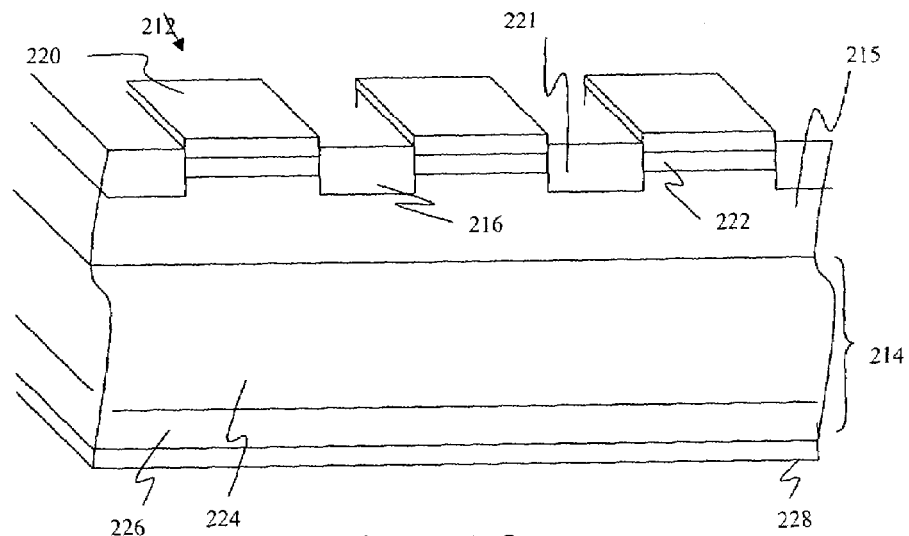
FIG. 10 is an enlarged, cross-sectional, perspective view of a portion of the quantum detector array of FIG. 9.

As best shown in FIG. 10, sensor layer 215 includes a plurality of sensor elements 212. Sensor layer 215 comprises an epitaxial layer preferably made of silicon, although it should be understood that other semiconductor materials may be selected, such as gallium arsenide, germanium, gallium nitride, etc. Sensor elements 212 comprise a $n^+$-type region or layer 220, and a p-type region or layer 222 immediately adjacent to $n^+$-type region 220 to establish a pn junction. (The terms "layer" and "region" are used interchangeably herein.) Creation of $n^+$-type region 220 and p-type region 222 may be accomplished, for example, using standard doping and/or lithographic techniques. In the interest of brevity, this detailed description refers to the illustrated pn junction as depicted in FIG. 10, although it should be understood that other arrangements are possible. For example, the placement of $n^+$-type region 220 and a p-type region 222 may be transposed, so that in FIG. 10 region 222 rests on top of region 220. Corresponding modifications to the doping charges of layers 224 and 226 (discussed below) would be made to accommodate this transposition, as is known in the art.

Sensor elements 212 are illustrated as possessing a square shape, possessing dimensions of approximately 20 microns by approximately 20 microns, for example, although other shapes and dimensions may be selected. In a particularly preferred embodiment of the invention, each sensor element 212 constitutes an avalanche photodiode, preferably operating in non-linear breakdown mode.

Quantum detector array 210 illustrated in FIG. 9 is represented by a three-by-three matrix of sensor elements 212 for purposes of simplification. Although not particularly limited, quantum detector array 210 of a photosensor may include, for example, between hundred(s) and thousand(s) of sensor elements 212, although fewer or more sensor elements 212 may be included in array 210. It is within the scope of the invention to provide a photosensor comprising a single sensor element 212. Further, the photosensor may possess sensor element 212 arrangements other than that depicted in FIG. 9. For example, the number of rows and columns of a photosensor may differ from one another. Sensor elements 212 may be arranged in a non-grid pattern, i.e., without set columns and/or rows. Sensor elements 212 alternatively may be arranged in a one-dimensional array or three-dimensional array. Sensor elements 212 may be mounted directly or indirectly on a single substrate 214 or on multiple substrates. Intervening layers may be interposed between substrate 214 and sensor layer 215.

A grid of trenches 216 is preferably formed in sensor layer 215 using known techniques, e.g., dry or wet etching, for separating the sensor elements 212 apart from one another. Generation of trenches 216 may involve a standard lithographic process, and may take place before or subsequent to doping of $n^+$-type regions 220 and p-type regions 222. Advantageously, trenches 216 are relatively narrow, and arranged between sensor elements 212 to consume relative small amounts of horizontal area. As depicted in FIG. 10, trenches 216 extend within sensor layer 215 to a depth beyond n⁺-type regions 220 and p-type regions 222, but do not penetrate completely through sensor layer 215. It is contemplated that trenches 216 may extend completely through sensor layer 215 and optionally into common substrate 214.

As best shown in FIG. 10, array 210 further comprises optical isolating elements 221 for optically isolating sensor elements 212 from one another so as to substantially reduce or eliminate optical cross-talk between sensor elements 212. (For simplification purposes, illustration of optical isolating elements 221 has been omitted from FIG. 9.) Optical isolating elements 221 comprise an optically non-conductive material, such as a polyimide or metal capable of substantially eliminating cross-talk, partially or completely filling trenches 216. Preferably, optical isolating elements 221 permit less than 1.0 percent, more preferably less than 0.1 percent of the photons generated during the avalanche process (discussed below) from traveling between individual sensor elements 212. The degree of optical and/or electrical isolation may be varied according to the preferred intended use, for example, by controlling the dimensions of trenches 216 and the selection of optical isolating elements 221. It should be understood that trenches 216 may be replaced with barriers, walls, or other structures or combinations of structures to reduce cross-talk between sensor elements 212. Further, trenches may be filled with alternative materials, or left unfilled.

As further illustrated in FIG. 10, relatively thick and lightly p-doped p-i (π) region 224 of common substrate 214 is situated below sensor layer 215. A p⁺⁺-type layer 226 of common substrate 214 is adjacent p-i region 224. Common electrode 228 is positioned below the exposed lower surface of p⁺⁺-type layer 26.

As best shown in FIG. 9, quenching elements 230 and common electrode 232 are arranged over trenches 216. (For simplification purposes, illustration of quenching elements 230, connectors 231, and common electrode 232 has been omitted from trenches 216 of FIG. 10.) It should be understood that quenching elements 230, common electrode 232, and/or connectors 231 may be positioned within trenches, such as buried within optical isolating elements 221. Common electrodes 228 and 232 are produced, for example, of a thin layer of metal (e.g., aluminum and/or titanium) or other suitable conductive material.

In FIG. 9, quenching elements 230 are shown in three columns extending in a front-to-rear direction on substrate 214. Common electrode 232 includes a main body portion (in FIG. 9 to the left of quenching elements 230) also extending in a front-to-rear direction. Two stem portions of common electrode 232 are depicted in FIG. 9 extending in a direction from side-to-side of substrate 214. Connectors 231 electrically interconnect a first row of quenching elements 230 to the front stem portion of common electrode 232. The second and third rows of quenching elements are located on opposite sides of and electrically interconnected (via connectors 231) to the rear stem portion of common electrode 232. As used herein, the term "interconnected" and derivatives of the term (e.g., interconnect, interconnecting) encompass both direct and indirect connections between elements, especially as the term is use in relation to electrical interconnections.

Figure 12:
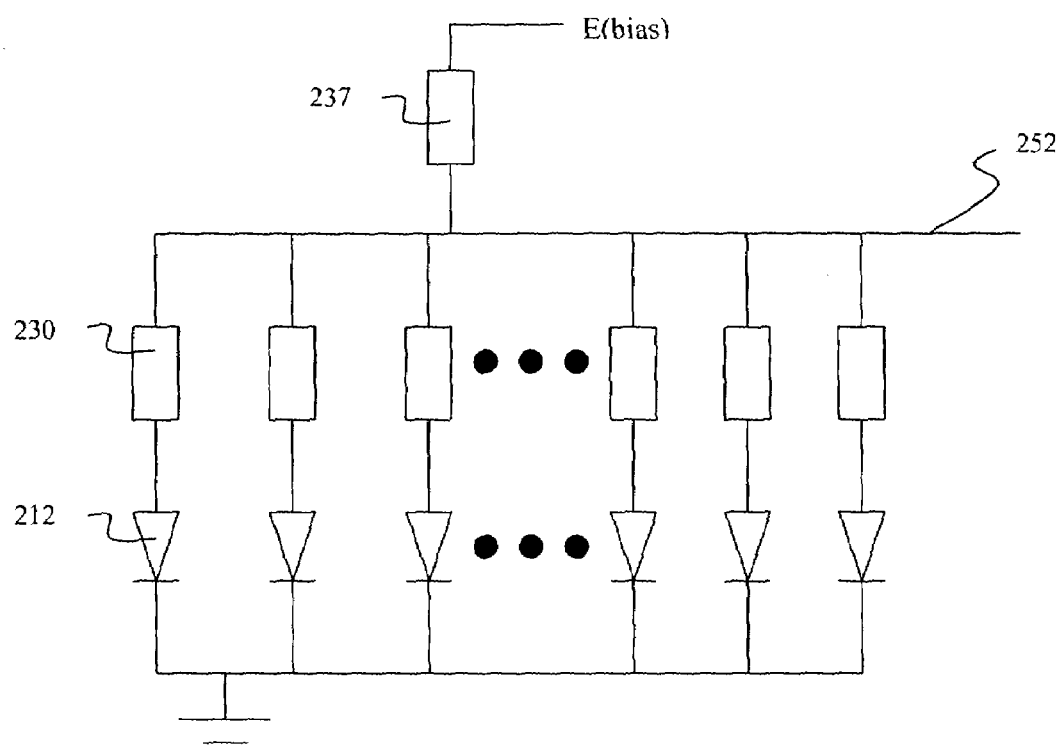
FIG. 12 is a sensor circuit diagram.

The sensor circuit of FIG. 12 is preferably operated in the so-called breakdown mode. Breakdown mode entails reverse-biasing the photodiode with a bias voltage $E_{bias}$ typically a few volts greater than the photodiode breakdown voltage, which is the voltage at which a single photon absorption produces complete electrical breakdown of the photodiode active region by impact ionization. Reverse bias voltage $E_{bias}$ may be applied from either of common electrodes 228, 252, i.e., it is within the scope of the invention to reverse polarity of the pixel. Reference numeral 237 represents a resistive or impedance component.

The breakdown mode in which sensor elements 212 are preferably operated produces a non-linear response, i.e., the response of a single sensor element 212 is not proportional to the number of photons absorbed by that single sensor element 212. The absorption of a single photon by a single sensor element 212 produces the same signal as the coincident absorption of multiple photons by the single sensor element 212, because the high reverse bias causes even a single photon to generate an avalanche leading to current saturation. It should be understood that the quantum detector preferably operates in the symmetric avalanche breakdown mode involving both type of carriers: (i.e., electrons and holes) in the impact ionization process.

The high sensitivity of avalanche photodiodes operated in breakdown mode can lead to false detection breakdowns. Specifically, a sensor element 212 can undergo spontaneous breakdown due to thermal generation of an electron-hole pair, resulting in the production of a dark rate signal (a signal contributing to dark current). It is highly desirable to provide a system that permits these spontaneous breakdowns responsible for dark rate signals to be identified and distinguished from breakdowns caused by receipt of electromagnetic radiation 211 (FIG. 13) from scintillator 213 or another intended source.

In the sensor circuit of FIG. 12, sensor elements 212 of photosensor 210 are arranged in parallel, with only a small number of sensor elements 212 shown for simplification purposes. A reverse bias voltage ($E_{bias}$) is applied to sensor elements 212 to increase the electric field in the depletion regions between n⁺-type regions 220 and p-type regions 222. The electric field created by the reverse bias is at a maximum at the pn junction, and then decreases slowly through p layer 222. The interaction of a quantum of electromagnetic radiation 211 released by an electromagnetic radiation-emission source 213 with sensor element 212 (e.g., via absorption of a photon or impact of a positron) excites an electron of sensor element 212 and generates an electron-hole pair. It is preferred to use a scintillator for the generation of photons. It is envisioned that other electromagnetic radiation sources 213 and other forms of ionizing radiation (e.g., ionization particles) may be used to fire the radiation-sensitive elements.

The nearly uniform field of the depletion zone separates the electron-and-hole pair, causing the electron and hole to be driven towards the n⁺ and p sides, respectively. When the drifting electron reaches the pn junction, the electron experiences the high electric field and accelerates and collides with the silicon atomic structure, releasing additional electrons and holes via secondary ionization, known as an avalanche. Thus, from a single photon entering the pn junction, a large number of electrons and holes can be generated and contribute to a photocurrent represented in FIG. 13 by reference numeral 238. The photocurrent output, i.e., analog signals 238 of a plurality of sensor elements 212 is collected as a summed analog signal 252.

FIG. 12 illustrates each sensor element 212 arranged in series with a respective quenching element 230. Quenching elements 230 are provided to stop the avalanche process. Essentially, quenching elements 230 function in a passive mode to reset sensor elements 212 to an off state. Preferably, each sensor element 212 is electrically interconnected via connector 231 to a respective quenching element 230. Preferably, quenching elements 230 are produced by complementary metal-oxide-semiconductor (CMOS)-compatible technology, preferably using poly-silicon (or alternatively silicon carbide) for reaching the high resistive values required for effective quenching. It should be understood that various quenching devices may be selected for use with the present invention, including active quenching devices (e.g., triggerable circuits).

As best shown in FIG. 9, quenching elements 230 are positioned to provide for a high likelihood that ionizing radiation, such as photons from scintillator 213, will reach the active area of sensor elements 212 without absorption by quenching elements 230. In this regard, quenching elements 230 preferably are located in trenches 216 immediate adjacent to their respective sensor elements 212. As arranged in the illustrated embodiment, a pathway between a radiation-emission source (e.g., scintillator) 213 (FIG. 13) and the radiation-receiving surfaces of sensor elements 212 is left at least partially unobstructed by quenching elements 230, so that at least a portion of the radiation-receiving surface within the pathway is not overlapped or physically obstructed by quenching elements 230. This arrangement increases the sensitivity of the sensor elements 212 to light wavelengths that could otherwise be substantially absorbed by the passive quenching elements or other resistive layers. It should be understood that quenching elements 230 may partially cover the radiation-receiving surface of sensor elements 212, e.g., less than 10 percent of the surface area, so long as a sufficient region of radiation-sensitive surfaces of sensor elements 212 is left accessible for receiving radiation from the radiation-emission source at a high efficiency. Typical measurements of quantum efficiency for avalanche photodiode elements are above 70%. Preferably, however, quenching elements 230 are positioned completely outside of the radiation-receiving surface of sensor elements 212, so that quenching elements are not within the pathway between the radiation emission source 213 and the radiation-receiving surface.

It should be understood that although resistive layers are preferably omitted from the direct path between the radiation-emission source and sensor elements 212, other materials that do not substantially affect (e.g., via absorption or reflection) the transmission and receipt of radiation particles by the radiation-receiving surfaces of sensor elements 212 may be formed, placed, or otherwise positioned in this direct path.

Figure 11:
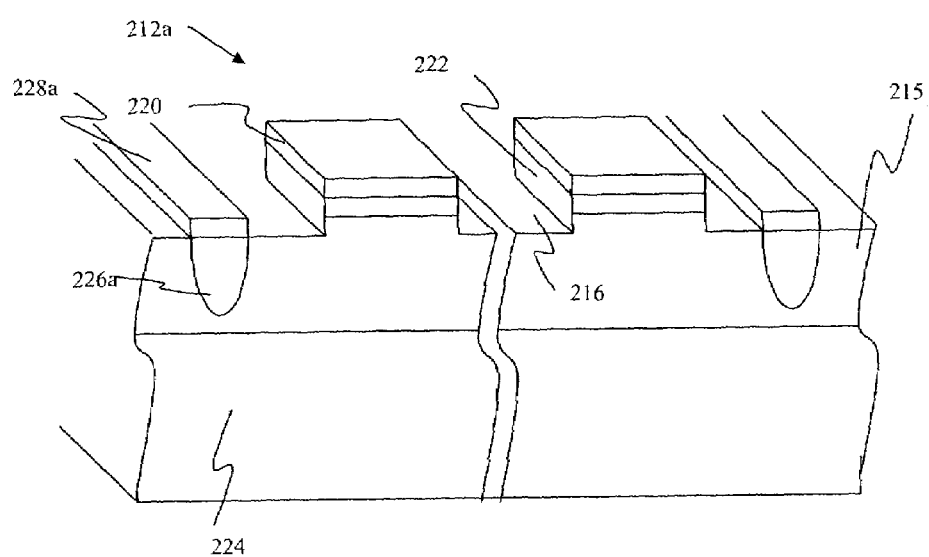
FIG. 11 is an alternative embodiment of a portion of a quantum detector array shown in cross-sectional, perspective view.

Modifications and variations to the semiconductor and sensor circuit architecture are within the scope of the invention. For example, FIG. 11 illustrates an alternative embodiment in which $p^{++}$ zone 226a is located in a well adjacent to trenches 216 of the semiconductor. Preferably, the well and $p^{++}$ zone 226a surround detector array 210. Still another modification of the semiconductor architecture shown in FIG. 11 involves application of a common electrode 228a material on top of $p^{++}$ zone 226a.

Fabrication techniques, including epitaxial deposition and doping procedures, are known in the art and can be practiced to make the photosensors described herein.

Meta-Arrays and Quantum Photosensor Read-Out Systems

Returning to FIG. 3A, preferably an equal number of scintillators 80 and photosensors 84 is provided in a meta-array of a camera sub-module. For example, as shown in FIG. 3A, a meta-array includes scintillator 80 and photosensor 84 pairs arranged in a matrix of four columns and two rows. Each photosensor 84 may comprise an array of sensor elements, e.g., 212 of FIGS. 9 and 10. It should be understood that meta-arrays may include a greater or lesser number of scintillator 80/photosensor 84 pairs, including as few as one pair, and as many as between hundred(s) and thousand(s) of pairs. Further, arrangements other than that depicted in FIG. 3A may be employed. For example, the number of rows and columns may differ from one another. Scintillators 80 and photosensors 84 may be arranged in a non-grid pattern, i.e., without set columns and/or rows. Scintillators 80 and photosensors 84 alternatively may be arranged in a one-dimensional array or three-dimensional meta-array.

Optical coupling between scintillators 80 and photosensors 84 may be attained in the illustrated embodiment by placing respective end surfaces of scintillator 80 and photosensor 84 of a pair into facing, optionally contacting relationship. Scintillator 80 may be a single crystal or multi-crystal elements sintered together. It should be understood that coupling materials, such as 82 in FIG. 3A, may assist in channeling the light from scintillator 80 into photosensor 84 by matching the refractive indices of the optical surfaces of scintillator 80 and photosensor 84. For example, photosensor 84 may possess an anti-reflective coating or other thin surface layer in order to obtain satisfactory optical coupling to the scintillator 80. End surfaces of scintillators 80 may be polished or roughened.

Carrier 86 may be made of ceramic material, although other suitable materials may be selected. Carrier 86 contains contacts or holes for transmitting signals, e.g., analog signals, from photosensors 84 to readout elements on the undersurface of the ceramic carrier 86, shown in FIG. 3B. Alternatively, photosensors 84 can include internal circuit elements within its physical housing so that the signals transmitted through carrier 86 are digitized.

The signals from each scintillator/photosensor 80/84 pair may be digitized within the physical confines of the photosensor, e.g., as shown in FIG. 3A, or in a separate physical element. In either embodiment, the signals of each scintillator/photosensor 80/84 pair preferably are digitized separately from other scintillator/photosensor 80/84 pairs. In this way, there is minimal or no interference between signals from one scintillator 80 to another, thereby allowing the PET apparatus operator to employ scintillators that have fairly long decay times (e.g., lutetium aluminum garnet, with a decay time of several microseconds).

Referring now more particularly to the bottom view of the meta-array depicted in FIG. 3B, trace 40 may comprise wires and/or contacts for transmitting signals from photosensors 84 through holes 42 in carrier 86. Traces 40 transmit electric signals from photosensors 84 to circuit element 43. Circuit element 43 preferably comprises a separate preamplifier for each photosensor 84. Signals amplified by the preamplifier of circuit element 43 are transmitted to an internal multiplexer of circuit element 43. The multiplexed signals are then sent through a bus or wire 45 to a buffer and/or computing element (such as a field-programmable gate array or microprocessor) 47, whose signals are then sent to a bus 48 for forwarding to a computer for analysis. It is understood that logic and/or processing elements such as track-and-hold, shaper, counter, and/or comparator circuitry may be included in circuit elements 43 and/or 47.

Buffer and/or computing element 47 preferably record(s) the time of each scintillation event with respect to a master clock in the array, and may also include calibration elements as needed or desired to correct for varying performances among the scintillators 80 and photosensors 84. Such calibration elements may include digital-to-analog converters capable of providing threshold voltages to comparators in circuit element 43. The construction of circuit element 43 is known, for example as published on Jun. 28, 2004 by scientist Felix Sefkow in the CALICE project at the high energy physics experiment DESY entitled "Front end electronics for the tile HCAL prototype". Computer analysis of the signals generated by one or more photosensors 84 in the meta-array is performed as is known for medical imaging devices.

In an alternative embodiment, one or more circuit elements of FIG. 3B may be eliminated from the bottom surface of carrier 86, and the element instead included in the physical housing of each photosensor 84.

Figure 13:
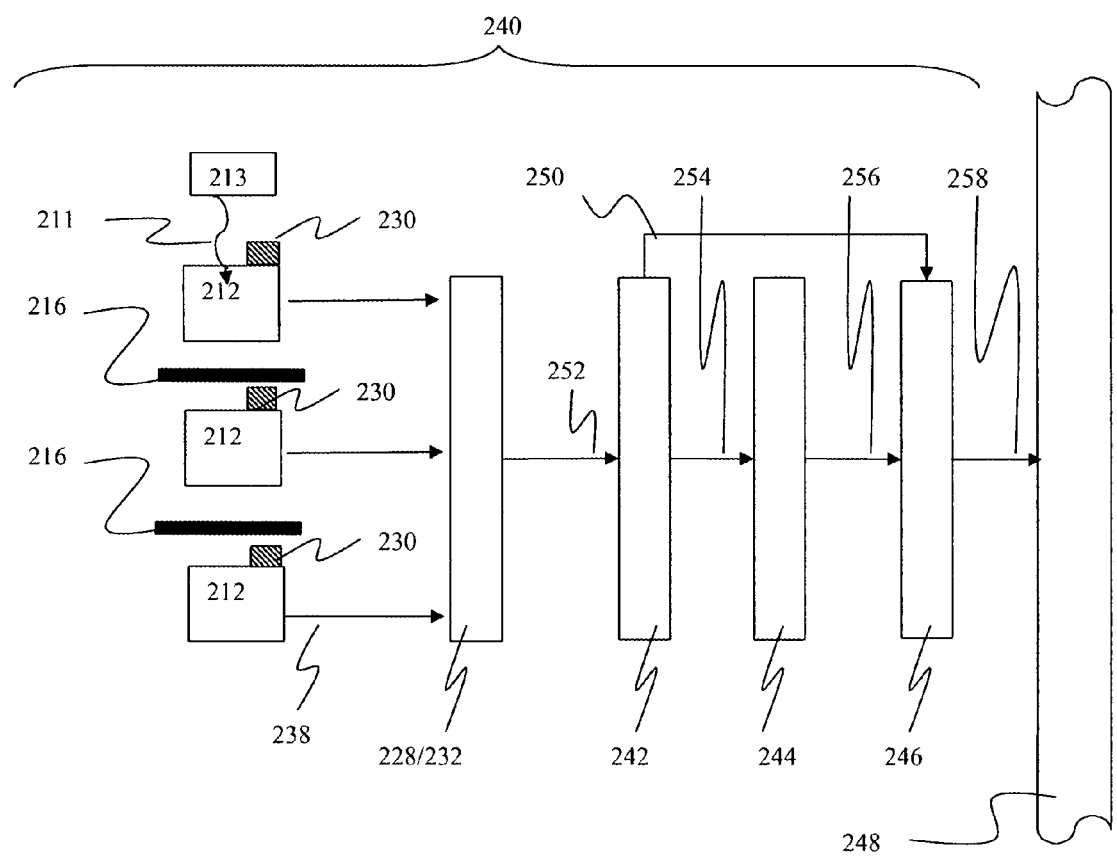
FIG. 13 is a flow diagram of a detector system incorporating the quantum detector array of FIG. 9, according to an embodiment of the invention.

FIG. 13 illustrates another embodiment of a read-out system 240 for generating and processing analog signals 238 generated by the breakdown of sensor elements 212. Analog signals 238 accumulate via common electrode 228 or 232 to produce a summed signal 252, which is sent to an interconnected discriminator 242, preferably via direct contact, or alternatively via one or more connecting structures. Discriminator 242 serves to limit the effect of dark current, as described below.

The breakdown mode in which sensor elements 212 are preferably operated produces a non-linear response. The system of FIG. 13 provides a discriminator 242 for identifying and distinguishing spontaneous breakdowns (responsible for dark rate signals) from breakdowns caused by receipt of electromagnetic radiation 211 from scintillator 213 or other intended sources. Discriminator 242 compares summed signal 252 to a threshold value, which is set to correspond to the discharge value of a sensor element 212.

When a scintillator 213 is activated, e.g., caused by receipt of a gamma ray, a shower of photons created by scintillator will simultaneously fire a plurality of sensor elements 212. If the summed signal 252 of the simultaneously fired sensor elements 212 possesses a value, e.g., current, exceeding the threshold value, then summed signal 252 is interpreted as signifying the coincident breakdown of two or more sensor elements 212, as would occur upon incidence of multiple photons from a scintillator absorbing a gamma ray. On the other hand, if summed signal 252 does not exceed the threshold value, then summed signal 252 is interpreted as having been produced by the breakdown of a single sensor element 212, without the coincident breakdown of additional sensor elements. The absence of coincident breakdowns from sensor elements 212 of a single photosensor 210 is uncharacteristic of a scintillator-induced event. Rather, the spontaneous discharges of sensor elements 212 leading to dark current are events that occur independently of one another. It is unlikely that a dark-current breakdown of multiple sensor elements 212 will occur simultaneously. It is therefore presumed that a summed signal 252 that does not exceed the threshold value was the result of a spurious spontaneous breakdown of a single sensor element 212, and may be dismissed.

Figure 15:
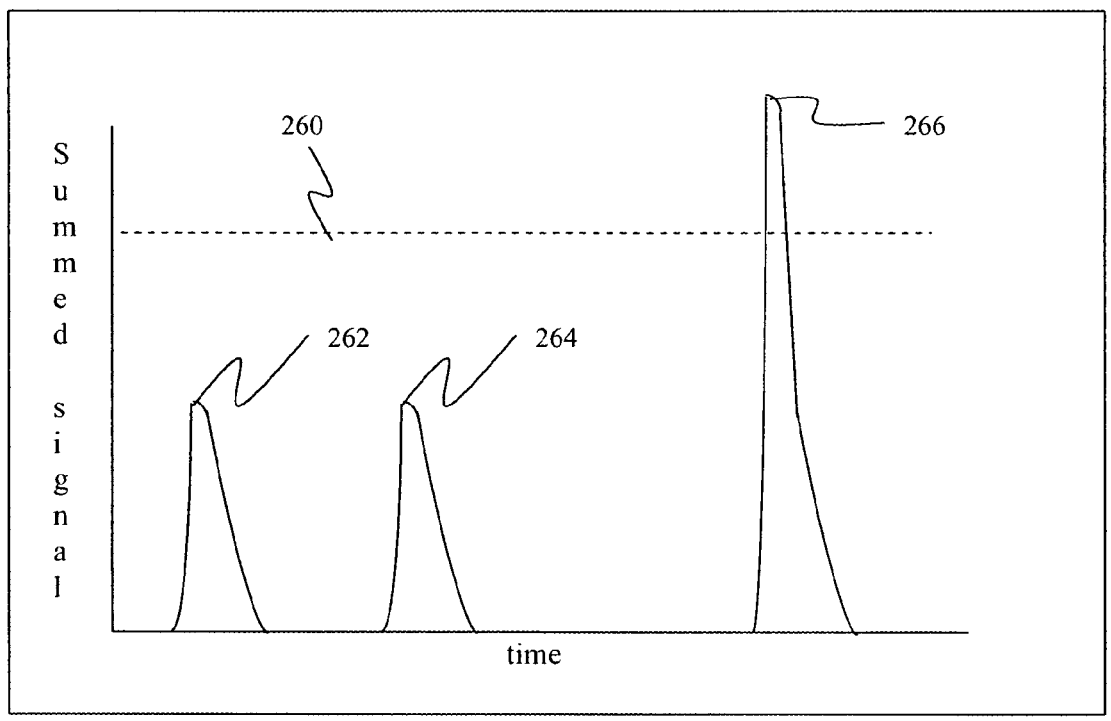
FIG. 15 is a graph showing summed analog signals generated by a quantum detector array for presentation to the discriminator of the system of FIG. 13.

FIG. 15 is an explanatory graph for demonstrating the rationale behind employing a threshold value for discriminating dark-current contributing discharges. The axes of FIG. 15 represent time (abscissa) and current or voltage (ordinate), as might be observed by an oscilloscope whose input electrode is set at the common electrode 228 or 232 with respect to ground potential. Line 260 represents a threshold value set at a value greater than the discharge value (current or voltage) of a single sensor element 212, but less than the discharge value of two sensor elements 212. Peaks 262, 264 are below threshold value 260, and thus are presumed to be caused by spontaneous firings of sensor elements 212 related to dark current. The frequency of such spontaneous breakdown peaks will be determined by the temperature of sensor elements 212, the purity of the semiconductors, and other factors. Discriminator 242 discards signals (252) corresponding to peaks 262, 264 having a voltage less than threshold value 260, dismissing such signals (252) as dark current. On the other hand, when many quanta of light are absorbed by multiple sensor elements 212 coincidently, as would occur if a shower of light photons was generated by a scintillator absorbing a gamma-ray, the currents from the individual radiation-sensitive elements sum, creating a signal (252) with a peak 266 that is above pre-set threshold 260. It may be observed that peaks 262, 264, 266 have rise-times defined by the breakdown time of sensor element(s) 212, and a decay-time defined primarily by the action of quenching element(s) 230.

If the summed signal 252 meets or exceeds the threshold value, e.g., corresponding to activation of two or more radiation-sensitive elements within a timing window, then discriminator 242 issues an output signal 254 for initiating analog-to-digital conversion in an analog-to-digital converter (ADC) 244, as shown in FIG. 13. It should be understood that the threshold value may be set to correspond to the discharge value of two, three, or more sensor elements 212, or other values, depending upon the application.

ADC circuit 244 sends digitized sum signal 256 to an interconnected buffer 246, via direct connection or alternatively via one or more connecting structures. Signals 258 are then relayed to data-bus 248 for forwarding to a computer processor for analysis and further processing.

Preferably, upon trigger of discriminator circuit 242, a timing signal 250 is generated and sent to a data buffer 246 by either direct contact or one or more connecting structures, in order to generate timing information associated with output signal 258. Alternatively, upon triggering of discriminator 242, a timing clock signal may generate a timestamp delivered to buffer 246.

Figure 14:
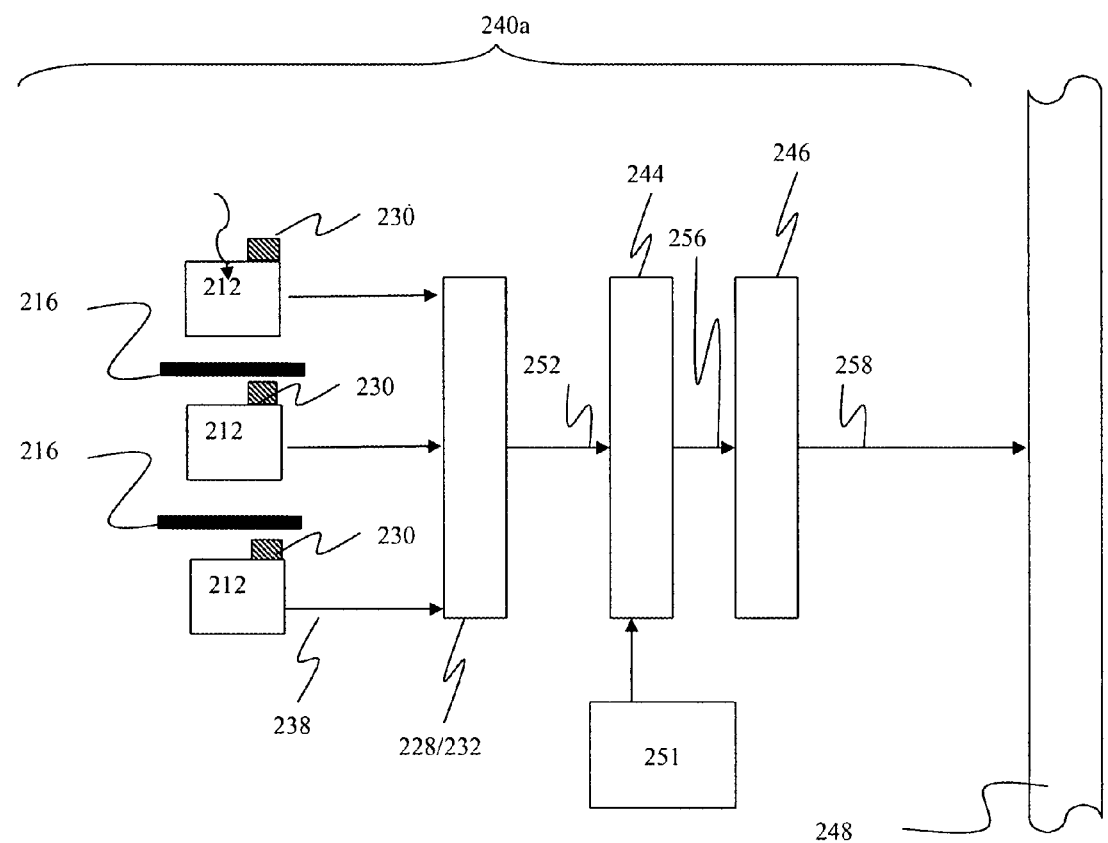
FIG. 14 is a flow diagram of a detector system incorporating the quantum detector array of FIG. 9, according to another embodiment of the invention.

In another system 240a shown in FIG. 14, ADC 244 is free running, so as to not require a trigger to initiate digitization, and an external clock 251 is provided for associating timing information with output signal 258. Although discriminator 242 is not present in FIG. 14, the discrimination function can be carried out using digital signal processing. Digitized summed signal 256 has a value proportional to the number of quanta absorbed by the array of sensor elements 212, with the dynamic range of the output signal affected by the number of quanta and the number of sensor elements 212 in the array. Analog-to-digital conversion may be accomplished based on voltage, charge, or time as the input signal as is known in the art. For example, time-over-threshold is a known analog-to-digital-conversion practice that may be implemented. The time above threshold value is a measure of an amount of time during which the monitored variable (e.g., current or voltage) exceeds the threshold during the sliding window of time. The pulse of a summed signal 252 representing two or more radiation-sensitive elements will exceed the threshold for a longer amount of time than a pulse of a signal representing the spontaneous, independent firing of a single radiation-sensitive element.

Many variations and modifications may be made to systems 240 and 240a. The read-out and computing elements performing the digital signal processing can reside on the same or different substrate/physical package as the sensor elements. ADC circuit 244 may be in operation all the time ("flash ADC"), wherein signal 254 serves as a trigger to ADC circuit 244, causing ADC circuit 244 to send a corresponding appropriate digital signal to buffer 246. As another alternative, the analog-to-digital conversion can be implemented though a latch/counter or flip-flop circuit, which would be substituted for ADC 244 in system 240 or 240a. An example of a latch/counter circuit is described in U.S. Patent Application Publication 2005/0224903. Still another option is to eliminate buffer 246, and instead deliver the timing signals 250 from discriminator 242 and signals 256 from analog-to-digital converter (ADC) 244 directly to data-bus 248.

Figure 16:
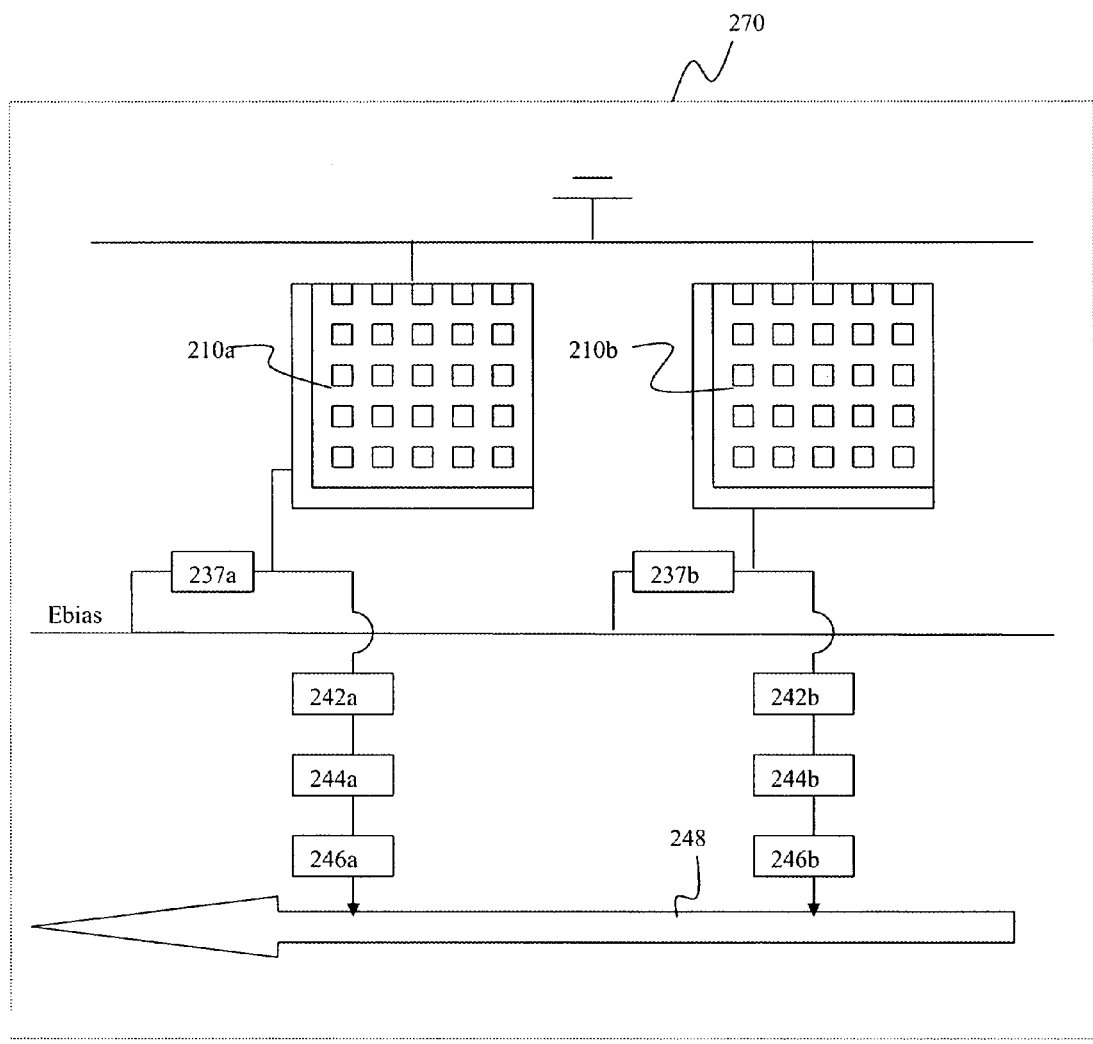
FIGS. 16 and 17 illustrate alternative embodiments of meta-arrays.

As shown in FIG. 16, the read-out components (i.e., discriminator 242, ADC 244, and buffer 246) may reside on the same chip, package, or substrate as a respective array 210, similar to the embodiment shown in FIG. 3B and described above. In FIG. 16, discriminator 242a, ADC 244a, and buffer 246a are associated with array 210a, located on a common chip 270. Discriminator 242b, ADC 244b, and buffer 246b are associated with array 210b, also located on the same common chip. The output signals are delivered to data bus 248.

The mounting of a plurality of arrays 210a, 210b, etc. on a common chip 270 as shown in FIG. 16 establishes a meta-array, i.e., an array of arrays 210. It should be understood that one, tens or hundreds, and perhaps thousands of pixels/arrays 210 may be assembled into a meta-array on a common chip 270 or other substrate. For example, camera sub-module 68 of FIG. 2 includes a meta-array of sixty-four (8×8) photosensors 84, each optically coupled to a respective scintillator 80.

Figure 17:
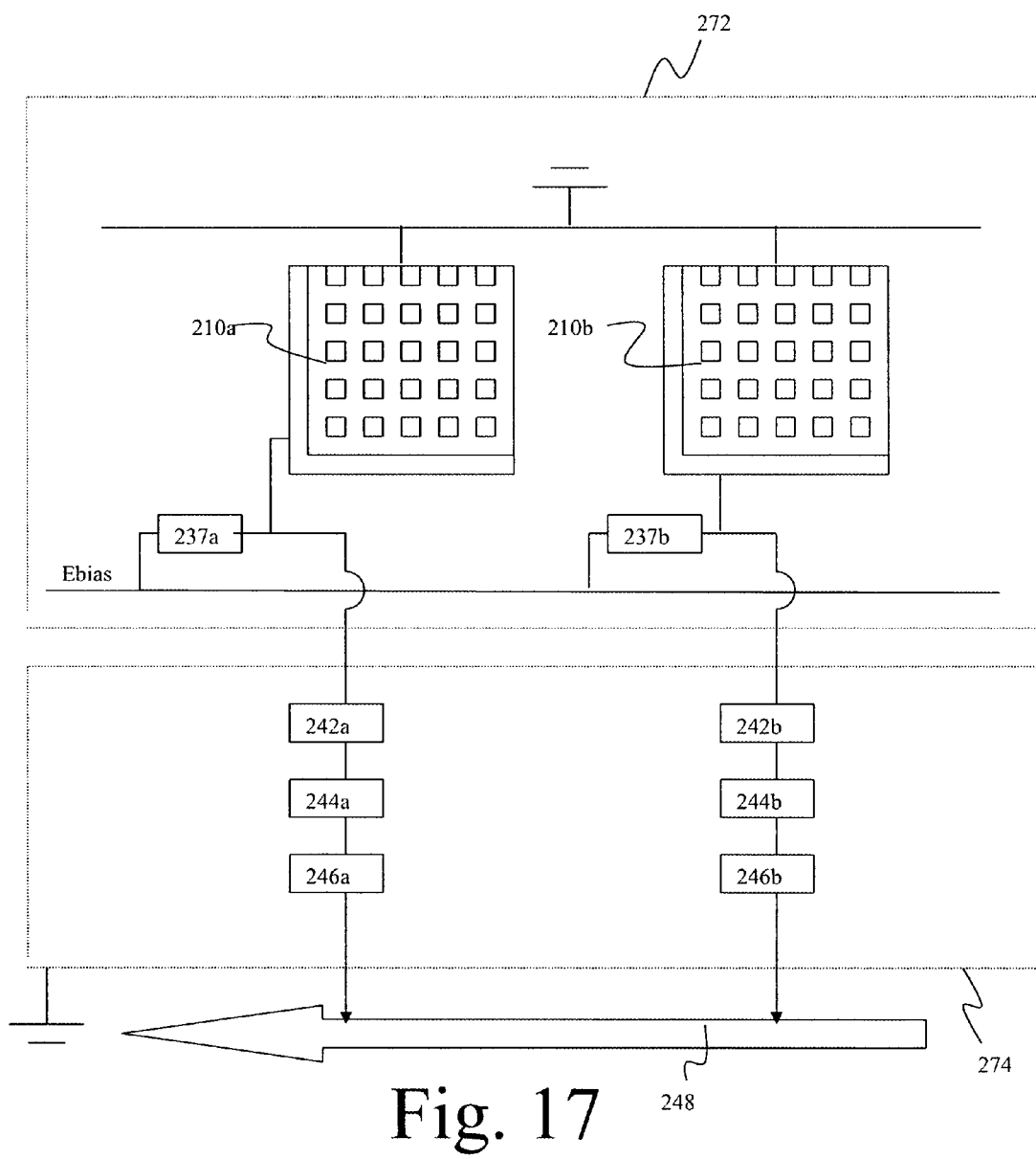

FIG. 17 illustrates an alternative embodiment in which arrays 210a, 210b of a meta-array are located on a first chip or substrate 272, and read-out components 242a, 244a, 246a, 242b, 244b, 246c, etc. reside on a separate second chip or substrate 274. Various other arrangements may be practiced. For example, any one or combination of components 242a, 244a, 246a, 242b, 244b, 246b, etc. may reside on substrate 270/272 with the remaining components residing on other substrate(s) or other package(s).

FIGS. 16 and 17 each illustrate meta-arrays comprising two, three, or more quantum detector arrays, wherein each quantum detector array 210 constitutes a pixel or photosensor of the meta-array. For example, a meta-array may possess one hundred quantum detector arrays (or "pixels") arranged in a ten-by-ten matrix of quantum detector arrays on a single wafer, e.g. 270 or 272. The arrangements described above and depicted in FIGS. 16 and 17 are meant to be illustrative, not exhaustive. Meta-arrays may feature quantum detector arrays 210a, 210b arranged in various arrangements, such as one-, two-, or three-dimensional arrangements.

The quantum detector arrays, meta-arrays, and optical read-out systems described herein can be used for various applications, for example, as parts of a camera sub-module of a medical imaging apparatus for applications such as positron emission tomography (PET), single photon emission computed tomography (SPECT), or x-ray computed tomography (CT). Techniques known in the art may be practiced to fabricate and assemble the optical read-out systems and other components of the imaging apparatus.

An advantage of certain embodiments described herein is the provision of a quantum detector with a novel arrangement of radiation-sensitive detector elements and quenching elements to achieve high geometric efficiency and improved sensitivity to light over a broad light range.

Another advantage of certain embodiments described herein involves the ability to read-out an array of quantum detectors to discriminate between, on the one hand, randomly occurring spontaneous discharges that contribute to dark current and, on the other hand, coincident discharges from multiple sensor elements (e.g., tiles) absorbing a shower of photons from an associated scintillator.

Scintillators

An embodiment of a scintillator, e.g., 80, 213, that may be employed in connection with camera sub-module 68 (FIG. 2) and the systems described above follows. It should be understood that the scintillator described below may be implemented with camera sub-modules and systems other than those described above.

Scintillators of the following embodiment are made of a sintered material, and more preferably a sintered material that emits light having a wavelength that is attuned to the sensitive portion of photosensors. Particularly preferred for use in the present embodiment is lutetium aluminate garnet (LuAg or $Lu_3Al_5O_{12}$), which emits light in the green range, within a wavelength of approximately 470-650 nanometers. The production of lutetium aluminate garnet is described in "Cerium-doped lutetium aluminum garnet optically transparent ceramics fabricated by a sol-gel process", by Xue-Jian Liu et al., in J. Mater. Res. Vol. 21, No. 6, June 2006, pages 1519-1525, the disclosure of which is incorporated herein by reference. Generally, sintered scintillators are prepared from a powder and usually a binder that are sintered at temperatures, for example and not necessarily by limitation, in the range of about 1500° C. to about 1800° C.

In FIG. 2, scintillators are illustrated as individual crystals 80 spaced from one another. It should be understood that scintillators may be formed from a block or slab of scintillator material with perpendicular cuts made in the slab to divide the scintillator material slab into individual component scintillators. Although not shown, optical isolating elements may be placed between scintillators. The optical isolating elements may comprise, for example, metal or polyimide barriers or "paint." The construction of scintillator crystals from a slab of scintillator material is described, for example, in U.S. Pat. No. 5,453,623, which is incorporated herein by reference.

Scintillators operate by responding to the absorption of a high energy photon, such as a gamma ray emitted from the body of a patient on bed 52, by emitting a flash of photon energy. More specifically, the photon absorbed by scintillator elevates electrons of scintillator to an excited state. The electrons return to a lower energy state by emitting the flash of photon energy, which is in turn converted into electronic signals by the associated photosensor, e.g., 84. The decay time of the scintillator typically refers to the amount of time required for the intensity of the light emitted by the scintillator to decrease to about 36% of the maximum light intensity. As described above, generally sintered scintillators have a relatively long decay time, for example, of approximately 50 nanoseconds or longer, for example, approximately 50 nanoseconds to approximately 2000 nanosecond (e.g., approximately 50 to approximately 500 nanoseconds).

Because of these long decay times of the scintillators of certain embodiments of the invention, each scintillator may be optically coupled to one corresponding photosensor to channel light emitted from each scintillator to its corresponding photosensor only. Conversely, each photosensor preferably receives light only from its corresponding scintillator. The increase in expense resulting from this one-to-one association is offset by the lower cost of the sintered scintillator compared to a single crystal scintillator.

Photosensors used with the above embodied scintillators preferably are solid-state, high gain photosensors, such as sensors 210 described above. Gain is the number of electrons produced by photon absorption. Preferably, the gain of photosensor is at least 10,000. Photosensors may be operated in the so-called breakdown mode to produce a non-linear response, i.e., the response of photosensor is not proportional to the number of photons absorbed. The absorption of a single photon produces the same signal as the coincident absorption of multiple photons, because the high reverse bias causes even a single photon to generate an avalanche leading to current saturation. It should be understood that the quantum photosensor preferably operates in the symmetric avalanche breakdown mode, defined as involving both type of carriers (i.e., electrons and holes) in the impact ionization process. The photosensors may be constructed in the form of a pixel comprising a quantum detector array and electronics package described above in reference to FIGS. 9 through 17.

Position Sensing

The various embodiments above may be modified alone or in combination with one another to include position sensors, such as position sensor 99 illustrated in FIG. 2 and the position sensors of the glove described in reference to FIG. 8. According to an embodiment of the invention, position-sensors may be incorporated within or solidly affixed to the packages, in order to build a flexible system for imaging. Position detectors or sensors may be attached to any components of the system (e.g., panels, connector boards, or sub-modules) for additional flexibility in configuration of the system. Position sensors have been incorporated into many devices that are in wide use, including gloves as discussed above. The use of position sensors can be integrated into the data collection and reconstruction algorithm in a manner similar to the article "Flexible geometries for hand-held PET and SPECT cameras", published in the 2001 IEEE Nuclear Science Symposium Conference Record, Volume 2, 4-10 Nov. 2001 Page(s): 1133-1136, by Weinberg et al. or a variation thereof, e.g., in which the positions of sub-modules are known with respect to one another. Alternatively, the projections of gamma-rays emitted from radiation-emitting layer onto other panels may be used to determine relative positions of the panels to each other. Gloves for virtual reality applications are commercially available (e.g., CyberGlove), and are as described in U.S. Pat. No. 4,988,981, which is incorporated herein by reference.

Various benefits are derived from practicing embodiments described above. For example, in those embodiments, involving the contemporaneous detection of transmission and internally generated emissions, scanning time is reduced compared to conventional methods which stagger emission image scanning and attention image scanning. The shorter scanning period permits for scanning of a greater number of patients over a given time period. The shorter scanning periods are especially beneficial for those patients suffering from claustrophobia or other conditions that complicate the scanning procedure or make the patient uncomfortable. Additionally, contemporaneous acquisition of the transmission and internally generated emissions provides superior registration of the patient's position (attenuation image) with the patient's radiotracer distribution (emission image) for image registration.

While this invention has been described as having a preferred design, it is understood that it is capable of further modifications, uses and/or adaptations of the invention, following in general the principle of the invention and including such departures from the present disclosure as come within known or customary practice in the art to which the invention pertains, and as may be applied to the central features hereinbefore set forth, and fall within the scope of the invention of the limits of the appended claims.

What is claimed is:

1. A quantum detector array, comprising:
    a substrate;
    avalanche sensor elements situated on the substrate, the avalanche sensor elements having radiation-sensitive areas for detecting radiation from a radiation-emission source and adapted to operate in nonlinear breakdown mode in response to detected radiation; and
    quenching elements electrically interconnected to the avalanche sensor elements to stop the nonlinear breakdown of the avalanche sensor elements, the quenching elements positioned at least partially between the avalanche sensor elements to leave at least portions of the radiation-sensitive areas available to detect the radiation without obstruction from the quenching elements.

2. The quantum detector array of claim 1, wherein the quenching elements are positioned completely outside of the radiation-sensitive areas to leave an entirety of the radiation-sensitive areas available to detect the radiation without obstruction from the quenching elements.

3. The quantum detector array of claim 1, further comprising reverse biasing means for operating the avalanche sensor elements in breakdown mode.

4. The quantum detector array of claim 1, further comprising optical isolating elements for optically isolating the avalanche sensor elements from one another so as to substantially eliminate optical cross-talk between the avalanche sensor elements.

5. The quantum detector array of claim 4, wherein the optical isolating elements are disposed in trenches positioned between the avalanche sensor elements.

6. The quantum detector array of claim 5, wherein the quenching elements are disposed within and/or above the trenches.

7. The quantum detector array of claim 6, further comprising first and second common electrodes, wherein at least one of the common electrodes is positioned within and/or above the trenches.

8. The quantum detector array of claim 1, wherein the quenching elements cover less than 10 percent of the radiation-sensitive areas.

9. The quantum detector array of claim 1, wherein the radiation-sensitive areas are free of covering materials that substantially absorb or reflect radiation.

10. A quantum detector and readout system, comprising:
    a quantum detector array, comprising
    a substrate;
    avalanche sensor elements situated on the substrate, the avalanche sensor elements having radiation-sensitive areas for detecting radiation from a radiation-emission source and adapted to operate in nonlinear breakdown mode in response to detected radiation; and
    quenching elements electrically interconnected to the avalanche sensor elements to stop the nonlinear breakdown of the avalanche sensor elements, the quenching elements positioned at least partially between the avalanche sensor elements to leave at least portions of the radiation-sensitive areas available to detect the radiation without obstruction from the quenching elements; and
    a readout system electrically interconnected to the quantum detector array for processing signals received from the quantum detector array.

11. The quantum detector and readout system of claim 10, wherein:
    the readout system comprises a discriminator for distinguishing spontaneous independent breakdowns of the avalanche sensor elements from coincident breakdowns of a plurality of the avalanche sensor elements caused by detection of radiation from the radiation emission source.

12. The quantum detector and readout system of claim 11, wherein the discriminator compares summed signals to a threshold value, wherein the summed signals are generated by the spontaneous independent breakdowns of the avalanche sensor elements or the coincident breakdowns of the plurality of the avalanche sensor elements.

13. The quantum detector and readout system of claim 12, further comprising an analog-to-digital converter electrically interconnected to the discriminator for converting the summed signals to digital signals having a value representative of the number of the avalanche sensor elements undergoing coincident breakdown.

14. The quantum detector and readout system of claim 10, wherein the readout system and the quantum detector array are situated on a common substrate.

15. The quantum detector and readout system of claim 10, wherein:
the readout system comprises a discriminator electrically interconnected to the quantum detector array for receiving the signals from the quantum detector array and associating timing information with the signals.

16. The quantum detector and readout system of claim 15, wherein the discriminator interprets the signal for distinguishing spontaneous independent breakdowns of the avalanche sensor detectors from coincident breakdowns of a plurality of the avalanche sensor elements caused by detection of radiation from the radiation emission source.

17. The quantum detector and readout system of claim 16, wherein the discriminator compares summed signals to a threshold value, wherein the summed signals are generated by the spontaneous independent breakdowns of the avalanche sensor elements or the coincident breakdowns of the plurality of the avalanche sensor elements.

18. The quantum detector and readout system of claim 17, further comprising an analog-to-digital converter electrically interconnected to the discriminator for converting the summed signals to digital signals having values representative of the number of the avalanche sensor elements undergoing coincident breakdown.

19. The quantum detector and readout system of claim 15, wherein the readout system and the quantum detector array are situated on a common substrate.

20. The quantum detector and readout system of claim 10, wherein:
the readout system comprises an analog-to-digital converter electrically interconnected to the quantum detector array for converting analog signals emitted by the quantum detector array to digital signals having a value representative of the number of the avalanche sensor elements undergoing coincident breakdown.

21. The quantum detector and readout system of claim 20, further comprising a clock for associating timing information with the digital signals.

22. The quantum detector and readout system of claim 20, wherein the readout system and the quantum detector array are situated on a common substrate.

23. The quantum detector and readout system of claim 10, wherein the quenching elements cover less than 10 percent of the radiation-sensitive areas.

24. The quantum detector and readout system of claim 10, wherein the radiation-sensitive areas are free of covering materials that substantially absorb or reflect radiation.

25. The quantum detector and readout system of claim 10, wherein the quenching elements are positioned completely outside of the radiation-sensitive areas to leave an entirety of the radiation-sensitive areas available to detect the radiation without obstruction from the quenching elements.

26. A quantum detector system, comprising:
a plurality of radiation-sensitive scintillators for emitting photons in response to detected radiation, the scintillators comprising multiple crystals sintered together; and
a meta-array of solid-state, semiconductor quantum photo sensors, each of the photosensors being operatively coupled to and paired with an associated one of the scintillators so that each one of the solid-state, quantum photosensors receives photons from only the associated one of the scintillators with which the solid-state, quantum photosensor is paired, and so that the photons emitted from each one of the scintillators are received only by the associated one of the solid-state, quantum photosensors with which the scintillator is paired.

27. An imaging apparatus, comprising:
one or more camera sub-modules, each of the camera sub-modules comprising the quantum detector system of claim 26.

28. A method of obtaining images, comprising:
administering a body with a positron-emitting radiotracer for producing positrons which interact with the body to generate internally-generated emissions of gamma rays; and
detecting the internally-generated emissions with the positron-emission tomography device of claim 26.

29. A method of detecting radiation, comprising:
detecting radiation with a plurality of radiation-sensitive scintillators and emitting photons in response to detected radiation, the scintillators comprising multiple crystals sintered together;
operatively coupling and pairing each scintillator of the plurality of radiation-sensitive scintillators with an associated solid-state, semiconductor quantum photosensor of a meta-array of solid-state, quantum photosensors, and
transmitting the photons from the scintillator only to the associated solid-state, quantum photosensor with which the scintillator is paired.

30. A quantum detector system, comprising:
a plurality of radiation-sensitive scintillators for emitting photons in response to detected radiation, the scintillators comprising multiple crystals sintered together; and
a meta-array of solid-state, semiconductor quantum photosensors operatively coupled to the scintillators.

31. A quantum detector and readout system, comprising:
a quantum detector array comprising avalanche sensor elements having radiation-sensitive areas for detecting radiation from a radiation-emission source and adapted to operate in nonlinear breakdown mode in response to detected radiation; and
a readout system electrically interconnected to the quantum detector array, the readout system comprising
a summing electrode for generating a summed signal proportional to the number of the avalanche sensor elements activated by detection of radiation from a radiation emission source or by spontaneous independently breakdown;
a discriminator for analyzing the summed signal to distinguish the summed signal as generated either by the detection of radiation from the radiation emission source or by the spontaneous independent breakdown;
an analog-to-digital converter operatively connected to the discriminator for converting the summed signal generated by the detection of radiation from the radiation emission source to a digital signal having a value representative of the number of the avalanche sensor elements having undergone coincident breakdown.

32. The quantum detector and readout system of claim 31, wherein the discriminator compares summed signals to a threshold value.

33. The quantum detector and readout system of claim 31, further comprising reverse biasing means for operating the avalanche sensor elements in breakdown mode.

34. The quantum detector and readout system of claim 31, further comprising optical isolating elements for optically isolating the avalanche sensor elements from one another so as to substantially eliminate optical cross-talk between the avalanche sensor elements.

35. The quantum detector and readout system of claim 34, wherein the optical isolating elements are disposed in trenches positioned between the avalanche sensor elements.

36. The quantum detector and readout system of claim 31, wherein the discriminator receives the signals from the quantum detector array and associates timing information with the signals.

37. The quantum detector and readout system of claim 31, further comprising a chip on which the quantum detector array and the readout system are both commonly situated.

38. The quantum detector and readout system of claim 31, wherein the quantum detector array further comprises quenching elements electrically interconnected to the avalanche sensor elements to stop the nonlinear breakdown of the avalanche sensor elements.

39. The quantum detector and readout system of claim 38, wherein the quenching elements are positioned at least partially between the avalanche sensor elements to leave at least portions of the radiation-sensitive areas available to detect the radiation without obstruction from the quenching elements.

40. The quantum detector and readout system of claim 38, wherein the quenching elements cover less than 10 percent of the radiation-sensitive areas.

41. The quantum detector and readout system of claim 38, wherein the radiation-sensitive areas are free of covering materials that substantially absorb or reflect radiation.

42. The quantum detector and readout system of claim 38, wherein the quenching elements are positioned completely outside of the radiation-sensitive areas to leave an entirety of the radiation-sensitive areas available to detect the radiation without obstruction from the quenching elements.

43. The quantum detector and readout system of claim 31, further comprising:
  optical isolating elements for optically isolating the avalanche sensor elements from one another so as to substantially eliminate optical cross-talk between the avalanche sensor elements, wherein the optical isolating elements are disposed in trenches positioned between the avalanche sensor elements; and
  quenching elements electrically interconnected to the avalanche sensor elements to stop the nonlinear breakdown of the avalanche sensor elements, wherein the quenching elements are disposed within and/or above the trenches.

* * * * *